United States Patent
Vleugels et al.

(10) Patent No.: US 11,786,655 B2
(45) Date of Patent: Oct. 17, 2023

(54) CONTEXT-SENSITIVE PREDICTIVE OPERATION OF A MEDICATION DELIVERY SYSTEM IN RESPONSE TO GESTURE-INDICATED ACTIVITY CHANGES

(71) Applicant: MEDTRONIC MINIMED, INC., Northridge, CA (US)

(72) Inventors: Katelijn Vleugels, San Carlos, CA (US); Neha J. Parikh, West Hills, CA (US); Lavie Golenberg, Sherman Oaks, CA (US); Louis J. Lintereur, Boise, ID (US)

(73) Assignee: MEDTRONIC MINIMED, INC., Northridge (CA)

( * ) Notice: Subject to any disclaimer, the term of this patent is extended or adjusted under 35 U.S.C. 154(b) by 277 days.

(21) Appl. No.: 17/118,957

(22) Filed: Dec. 11, 2020

(65) Prior Publication Data
US 2021/0178064 A1 Jun. 17, 2021

Related U.S. Application Data

(60) Provisional application No. 62/947,942, filed on Dec. 13, 2019, provisional application No. 62/948,007, filed on Dec. 13, 2019.

(51) Int. Cl.
*A61M 5/172* (2006.01)
*A61M 5/142* (2006.01)
(Continued)

(52) U.S. Cl.
CPC ........ *A61M 5/172* (2013.01); *A61M 5/14248* (2013.01); *G16H 20/17* (2018.01);
(Continued)

(58) Field of Classification Search
CPC .. A61M 5/172; A61M 5/14248; A61M 5/142; A61M 5/168; A61M 2205/52;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| CN | 114787932 A | 7/2022 |
| EP | 4073811 A1 | 10/2022 |
| WO | 2021119549 A1 | 6/2021 |

OTHER PUBLICATIONS

International Preliminary Report on Patentability dated May 17, 2022 in corresponding international application PCT/US2020/064703 (7 pages).

(Continued)

*Primary Examiner* — Manuel A Mendez
(74) *Attorney, Agent, or Firm* — Weaver Austin Villeneuve & Sampson LLP

(57) ABSTRACT

Gesture-informed patient management systems and related medical devices and operating methods are provided. A method of operating a medical device involves identifying a current operational context, predicting an occurrence of an event based at least in part on historical data associated with the patient and a correlation between the current operational context and the event, automatically configuring operation of the medical device to influence a physiological condition of the patient to account for the predicted occurrence of the event, and after configuring the operation of the medical device to account for the predicted occurrence of the event, automatically reconfiguring the operation of the medical (Continued)

device in response to detected gesture data influenced by an output of a sensing arrangement.

20 Claims, 10 Drawing Sheets

(51) Int. Cl.
    *G16H 40/67*     (2018.01)
    *G16H 20/17*     (2018.01)

(52) U.S. Cl.
    CPC ......... *G16H 40/67* (2018.01); *A61M 2205/18* (2013.01); *A61M 2205/502* (2013.01); *A61M 2205/52* (2013.01); *A61M 2205/8206* (2013.01); *A61M 2230/201* (2013.01); *A61M 2230/63* (2013.01)

(58) Field of Classification Search
    CPC ........ A61M 2230/63; A61M 2230/201; G16H 20/17; G16H 40/67
    See application file for complete search history.

(56) References Cited

U.S. PATENT DOCUMENTS

| | | | |
|---|---|---|---|
| 4,755,173 | A | 7/1988 | Konopka et al. |
| 5,080,653 | A | 1/1992 | Voss et al. |
| 5,097,122 | A | 3/1992 | Colman et al. |
| 5,391,250 | A | 2/1995 | Cheney, II et al. |
| 5,485,408 | A | 1/1996 | Blomquist |
| 5,505,709 | A | 4/1996 | Funderburk et al. |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,485,465 | B2 | 11/2002 | Moberg et al. |
| 6,544,212 | B2 | 4/2003 | Galley et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,659,980 | B2 | 12/2003 | Moberg et al. |
| 6,736,797 | B1 | 5/2004 | Larsen et al. |
| 6,749,587 | B2 | 6/2004 | Flaherty |
| 6,752,787 | B1 | 6/2004 | Causey, III et al. |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,817,990 | B2 | 11/2004 | Yap et al. |
| 6,932,584 | B2 | 8/2005 | Gray et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,621,893 | B2 | 11/2009 | Moberg et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Mair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2007/0123819 | A1 | 5/2007 | Mernoe et al. |
| 2010/0160861 | A1 | 6/2010 | Causey, III et al. |
| 2012/0266251 | A1 | 10/2012 | Birtwhistle et al. |
| 2015/0134356 | A1 | 5/2015 | Atlas et al. |
| 2017/0049383 | A1 | 2/2017 | McMahon et al. |
| 2017/0053552 | A1* | 2/2017 | Zhong .................. A61B 5/7405 |
| 2017/0188979 | A1 | 7/2017 | Volpe |
| 2017/0220772 | A1* | 8/2017 | Vleugels ................ G16H 50/70 |
| 2018/0169334 | A1 | 6/2018 | Grosman et al. |
| 2018/0174675 | A1* | 6/2018 | Roy ....................... A61M 5/145 |
| 2018/0178061 | A1 | 6/2018 | O'Larte et al. |
| 2019/0251456 | A1 | 8/2019 | Constantin et al. |
| 2020/0135320 | A1 | 4/2020 | Vleugels |
| 2020/0289373 | A1 | 9/2020 | Vleugels |
| 2021/0060248 | A1 | 3/2021 | Golenberg et al. |
| 2021/0060249 | A1 | 3/2021 | Golenberg et al. |
| 2021/0100951 | A1* | 4/2021 | Chase .................. A61B 5/4839 |
| 2021/0177345 | A1 | 6/2021 | Wu et al. |
| 2021/0178066 | A1 | 6/2021 | Monirabbasi |
| 2021/0178069 | A1 | 6/2021 | Grosman et al. |
| 2021/0183490 | A1 | 6/2021 | Roy et al. |
| 2021/0183491 | A1 | 6/2021 | Grosman et al. |
| 2021/0183522 | A1 | 6/2021 | Lintereur et al. |

OTHER PUBLICATIONS

International Search Report and Written Opinion dated Mar. 25, 2021, in Application No. PCT/US2020/064703.

U.S. Non-Final Office Action dated Nov. 16, 2022, in U.S. Appl. No. 17/120,055.

Extended European Search Report dated May 4, 2023 in Application No. EP23154072.5.

* cited by examiner

CONTEXT-SENSITIVE PREDICTIVE OPERATION OF A MEDICATION DELIVERY SYSTEM IN RESPONSE TO GESTURE-INDICATED ACTIVITY CHANGES

CROSS-REFERENCE TO RELATED APPLICATION

This application claims the benefit of U.S. Provisional Patent Application Ser. No. 62/948,007, which was filed on Dec. 13, 2019, and U.S. Provisional Patent Application Ser. No. 62/947,942, which was filed on Dec. 13, 2019, which are both incorporated by reference herein in their entirety.

TECHNICAL FIELD

The present technology is generally related to the control, operation, and adjustment of a medication delivery system in response to patient lifestyle events or activities detected using a gesture-based physical behavior detection system.

BACKGROUND

Medical therapy delivery systems, such as fluid infusion devices, are relatively well known in the medical arts for use in delivering or dispensing an agent, such as insulin or another prescribed medication, to a patient. A typical medication infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

Regulating blood glucose level is complicated by variations in the response time for the type of insulin being used along with each patient's individual insulin response. Furthermore, a patient's daily activities and experiences may cause that patient's insulin response to vary throughout the course of a day or from one day to the next. Thus, it is desirable to account for the anticipated variations or fluctuations in the patient's insulin response caused by the patient's activities or other condition(s) experienced by the patient. Managing a diabetic's blood glucose level is also complicated by the patient's consumption of meals or carbohydrates. Often, a patient manually administers a bolus of insulin at or around meal time to mitigate postprandial hyperglycemia. While undesirably increasing the burden on the patient for managing his or her therapy, manual errors such as miscounting carbohydrates or failing to initiate a bolus in a timely manner can also reduce the therapy effectiveness. Accordingly, there is a need to facilitate improved glucose control and reduce patient workload.

BRIEF SUMMARY

The subject matter of this disclosure generally relates to gesture-informed patient management systems and related medical devices and operating methods for controlling or adjusting delivery of a fluid or other medicament, such as insulin, in response to patient lifestyle events or activities detected using a gesture-based physical behavior detection system.

In one embodiment, a method is provided for operating a medical device capable of influencing a physiological condition of a patient using a sensing arrangement capable of detecting physical movement by the patient. The method involves identifying, by a control system associated with the medical device, a current operational context, predicting, by the control system, an occurrence of an event based at least in part on historical data associated with the patient and a correlation between the current operational context and the event, resulting in a predicted occurrence of the event, automatically configuring operation of the medical device to influence the physiological condition of the patient to account for the predicted occurrence of the event, and after configuring the operation of the medical device to account for the predicted occurrence of the event, automatically reconfiguring the operation of the medical device in response to detected gesture data influenced by an output of the sensing arrangement.

In another embodiment, at least one non-transitory computer readable medium having stored thereon program code instructions is provided. The program code instructions are configurable to cause at least one processor to identify a current operational context associated with operating a medical device capable of influencing a physiological condition of a patient, predict an occurrence of an event based at least in part on historical data associated with the patient and a correlation between the current operational context and the event, resulting in a predicted occurrence of the event, automatically configure operation of the medical device to influence the physiological condition of the patient to account for the predicted occurrence of the event, and after configuring the operation of the medical device to account for the predicted occurrence of the event, automatically reconfigure the operation of the medical device in response to detected gesture data influenced by an output of a sensing arrangement capable of detecting physical movement by the patient.

In yet another embodiment, a system is provided that includes a medical device that regulates delivery of fluid to a patient, a gesture detection system configured to generate gesture data for the patient, and configured to communicate the gesture data, and at least one controller that controls operation of the medical device. The at least one controller is configured to identify a current operational context, predict an occurrence of an event based at least in part on historical data associated with the patient and a correlation between the current operational context and the event, resulting in a predicted occurrence of the event, automatically configure a setting of the medical device for delivering the fluid to the patient based on the predicted occurrence of the event, and after configuring the setting of the medical device based on the predicted occurrence of the event, automatically reconfiguring the setting of the medical device based on the gesture data received from the gesture detection system.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
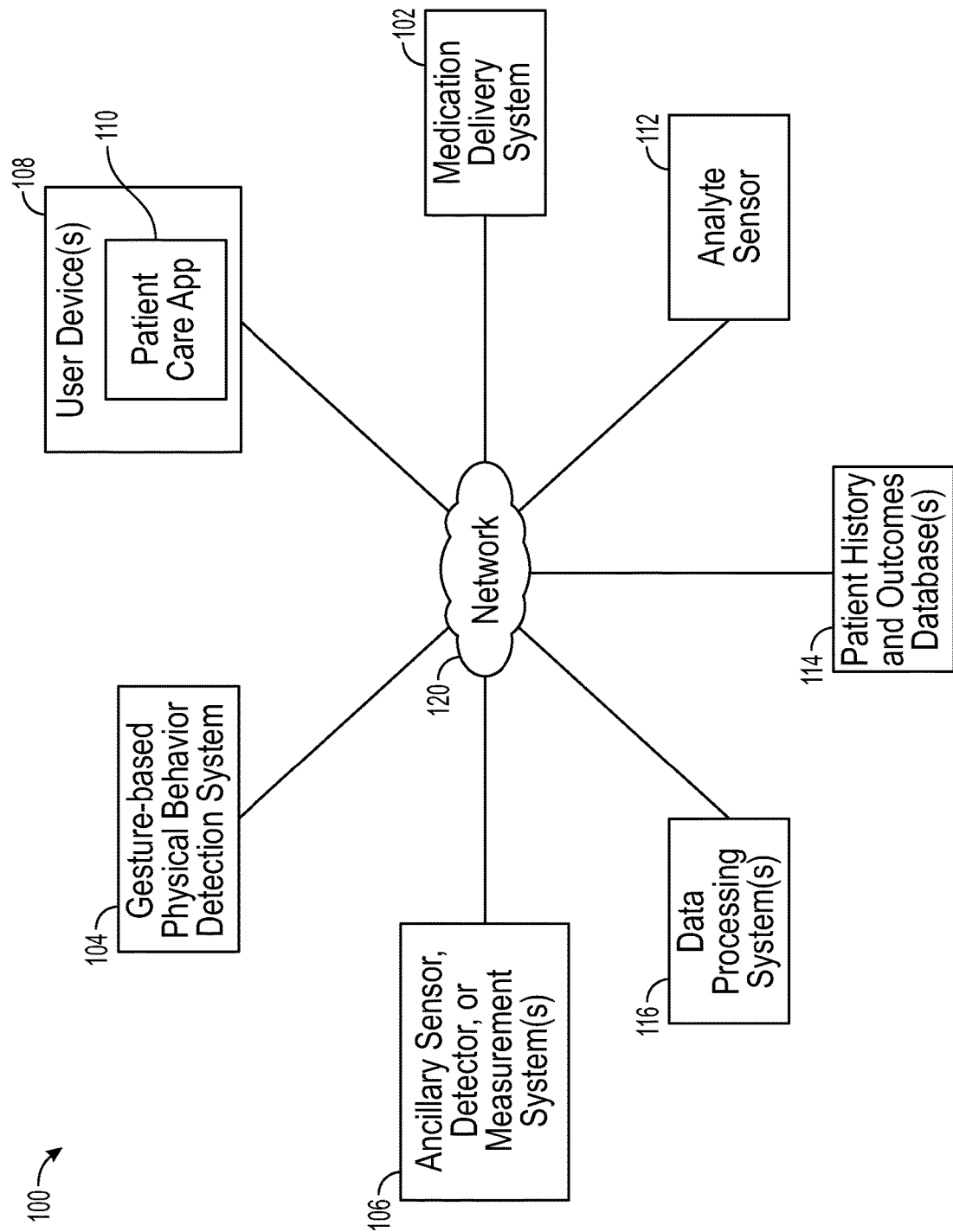
FIG. 1 is a simplified block diagram representation of an exemplary embodiment of a system that includes a medication delivery system that responds to changes in patient activity as indicated by the output of a gesture-based physical behavior detection system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more exemplary embodiments, the subject matter described herein is implemented in connection with a portable electronic medical device. Although many different applications are possible, for purposes of explanation, the following description may focus on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Program code instructions may be configurable to be executed by one or more processors, such as one or more digital signal processors (DSPs), general purpose microprocessors, controllers, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that regulates operation of a medication delivery system 102 or other medical device to thereby regulate a physiological condition of a patient user in response to events or other activities (e.g., eating, sleeping, exercise, and/or working, and/or the like) detected based on physical movements by the patient. In certain embodiments, the medication delivery system 102 responds to the patient's behavior as indicated by the output of a gesture-based physical behavior detection system 104 and/or the output of at least one ancillary sensor, detector, or measurement system 106 (hereinafter referred to as ancillary system(s) 106). Certain embodiments of the system 100 include, without limitation: the medication delivery system 102 (or device) that regulates delivery of medication to a patient user; at least one gesture-based physical behavior detection system 104 that monitors user behavior and/or status to obtain gesture data that indicates user activity events or behavior; at least one ancillary system 106; at least one user device 108 that includes or cooperates with a suitably written and configured patient care application 110;

an analyte sensor 112 to measure a physiological characteristic of the user, such that sensor data obtained from the analyte sensor 112 can be used to control, regulate, or otherwise influence the operation of the medication delivery system 102; and at least one patient history and outcomes database 114. In accordance with certain cloud-implemented embodiments, the system includes at least one data processing system 116, which may be in communication with any or all of the other components of the system 100. Other configurations and topologies for the system 100 are also contemplated here, such as a system that includes additional intermediary, interface, or data repeating devices in the data path between a sending device and a receiving device.

As described in greater detail below in the context of FIGS. 9-12, the system 100 may analyze historical patient data maintained in patient history and outcomes database 114 to predict when certain events or activities are likely to occur based on the operational context and perform contextual delivery adjustments at the medication delivery system 102 that are responsive to or otherwise informed by gestures detected by the gesture-based physical behavior detection system 104. For example, the occurrence of food intake events, exercise events, sleep events and/or the like may be predicted based on the historical patient data using the contextual data associated with historical occurrences of those events (e.g., based on recorded timestamps or time of day, day of the week, duration of the event, geographic location, etc.), other characteristics or attributes of those events (e.g., meal content, meal size, exercise intensity, sleep quality, etc.), potentially other data concurrent or contemporaneous to those events, such as measurement data provided by the analyte sensor 112 or another ancillary system 106. For example, the occurrence of an exercise event may be predicted to start within a certain time window in relation to the occurrence of a food intake event (e.g., relative to the start or end of a food intake event) based on historical correlations between the patient's prior exercise events in relation to the patient's prior food intake events. The relative degree of correlation between events may then be utilized to a confidence level to that prediction, which, in turn, may be assigned to any gestures consistent with that predicted exercise event within the given time window after the food intake event. By leveraging the correlation between the current operational context and the patient's historical event occurrences to increase the confidence assigned to the detected gestures, the medication delivery system 102 may respond more aggressively or proportionally to the confidence level to gestured events consistent with the patient's historical contextual behavior. Additional characteristics of a predicted event may also be determined based on correlations between the current operational context and the patient's historical event data, thereby allowing the medical delivery system 102 to adjust a medication dosing and/or medication dispensing schedule in a more informed manner in response to a detected gestured event based on the current operational context.

For example, if the medical delivery system 102 delivers insulin, a reduced insulin dosage or relaxed insulin delivery schedule and/or an increased target glucose value for determining insulin dosage commands may be determined for use by the medical delivery system 102 to decrease insulin delivery in a manner that is commensurate or proportional to the confidence level assigned a detected exercise event consistent with the current operational context given the historical contextual data associated with the patient's historical exercise events. In an equivalent manner, for a detected food intake event consistent with the patient's historical food intake behavior for the current operational context, the medical delivery system 102 may employ a more aggressive insulin delivery schedule or decreased target glucose value to determine insulin dosage commands for increasing insulin delivery in a manner that is commensurate or proportional to the confidence level/value assigned a detected food intake event.

Still referring to FIG. 1, at least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of medication delivery system 102 that is compatible with the features and functionality described here. For example, the medication delivery system 102 may be realized as a user-activated or user-actuated fluid delivery device, such as a manual syringe, an injection pen, or the like. As another example, the medication delivery system 102 may be implemented as an electronic device that is operated to regulate the delivery of medication fluid to the user. In certain embodiments, however, the medication delivery system 102 includes or is realized as an insulin infusion device, e.g., a portable patient-worn or patient-carried insulin pump, a smart insulin pen, or the like. In such embodiments, the analyte sensor 112 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Figure 2:
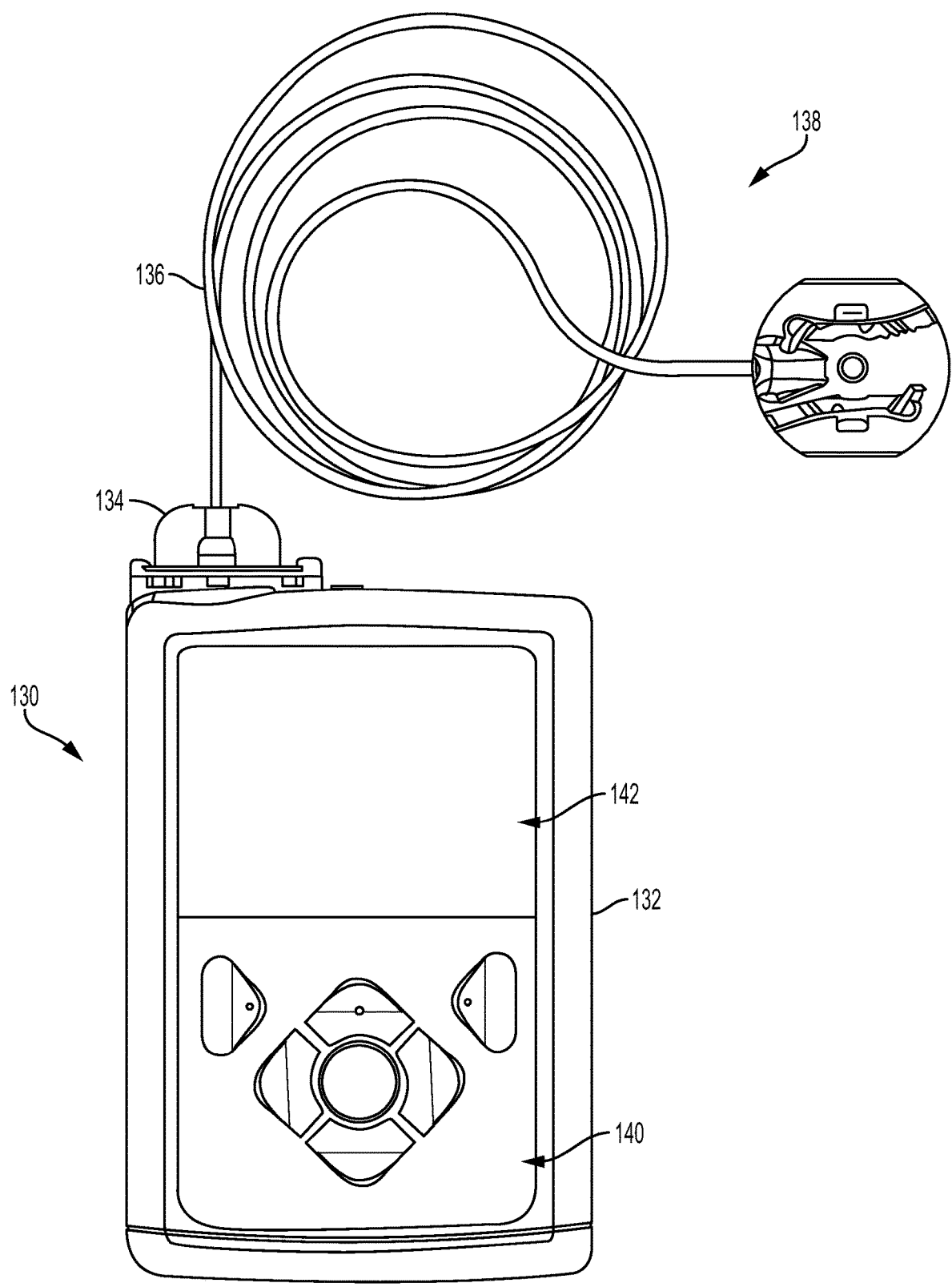
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3:
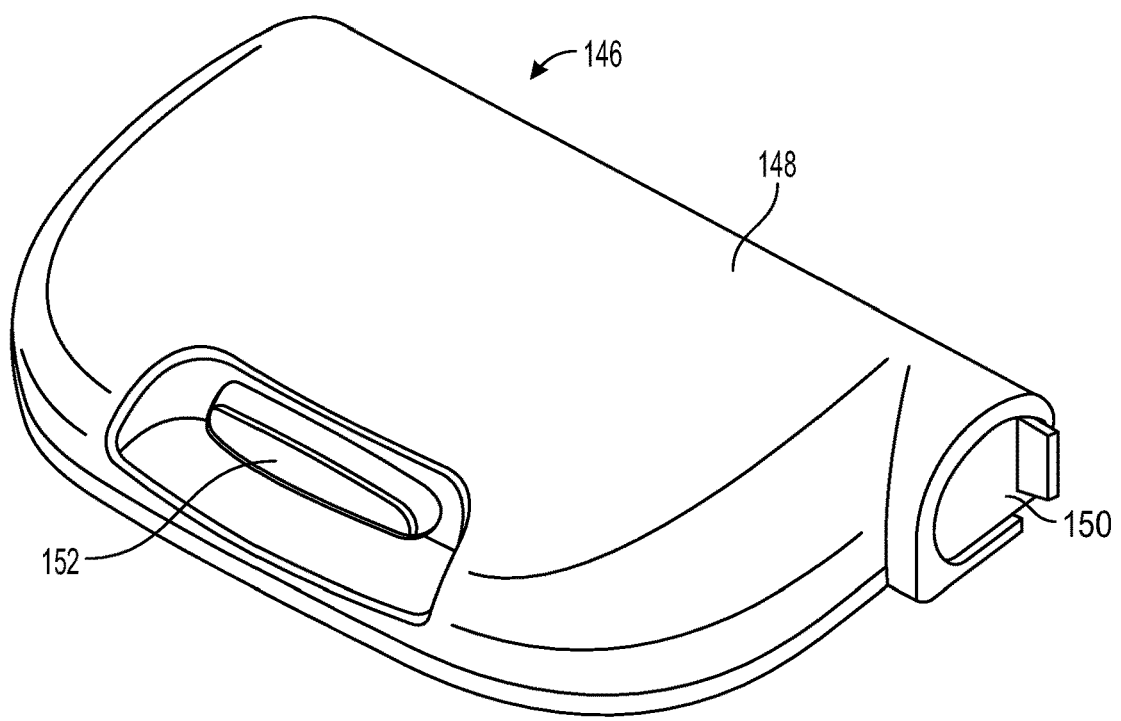
FIG. 3 is a top perspective view of an embodiment of an insulin infusion device implemented as a patch pump device that is suitable for use as the medication delivery system shown in FIG. 1.

FIG. 3 is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3). In such an implementation, the glucose sensor may take the place of the separate analyte sensor 112 shown in FIG. 1. The insulin infusion device 146 includes a housing 148 that serves as a shell for a variety of internal components. FIG. 3 shows the insulin infusion device 146 with a removable fluid cartridge 150 installed and secured therein. The housing 148 is suitably configured to receive, secure, and release the removable fluid cartridge 150. The insulin infusion device 146 includes at least one user interface feature, which can be actuated by the patient as needed. The illustrated embodiment of the fluid infusion device 146 includes a button 152 that is physically actuated. The button 152 can be a multipurpose user interface if so desired to make it easier for the user to operate the fluid infusion device 146. In this regard, the button 152 can be used in connection with one or more of the following functions, without limitation: waking up the processor and/or electronics of the fluid infusion device 146; triggering an insertion mechanism to insert a fluid delivery cannula and/or an analyte sensor into the subcutaneous space or similar region of the user; configuring one or more settings of the fluid infusion device 146; initiating delivery of medication fluid from the fluid cartridge 150; initiating a fluid priming operation; disabling alerts or alarms generated by the fluid infusion device 146; and the like. In lieu of the button 152, the insulin infusion device 146 can employ a slider mechanism, a pin, a lever, a switch, a touch-sensitive element, or the like. In certain embodiments, the insulin infusion device 146 may be configured and controlled to support other features and interactive functions described in more detail below.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

Figure 4:
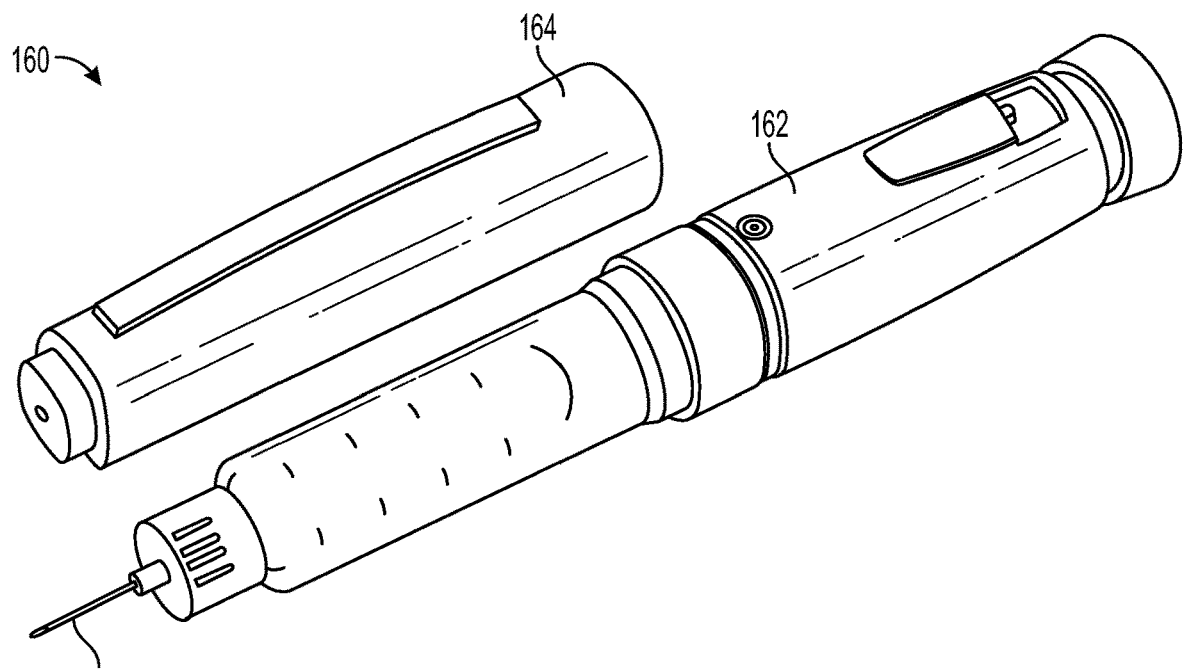
FIG. 4 is a perspective view of an exemplary embodiment of a smart insulin pen that is suitable for use as the medication delivery system shown in FIG. 1.

FIG. 4 is a perspective view of an exemplary embodiment of a smart insulin pen 160 suitable for use as the medication delivery system shown in FIG. 1. The pen 160 includes an injector body 162 and a cap 164. FIG. 4 shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 5:
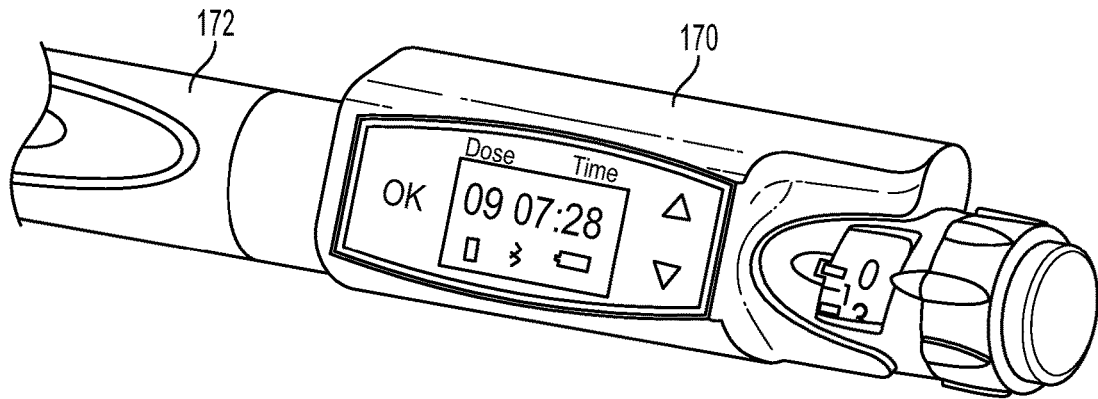
FIG. 5 is a perspective view of an exemplary embodiment of a smart pen accessory that is suitable for use with the medication delivery system shown in FIG. 1.

FIG. 5 is a perspective view of an exemplary embodiment of a smart pen accessory 170 that is suitable for use with the medication delivery system 102 shown in FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Referring again to FIG. 1, the analyte sensor 112 may communicate sensor data to the medication delivery system 102 for use in regulating or controlling operation of the medication delivery system 102. Alternatively, or additionally, the analyte sensor 112 may communicate sensor data to one or more other components in the system 100, such as, without limitation: a user device 108 (for use with the patient care application 110); a data processing system 116; and/or a patient history and outcomes database 114.

The system 100 can support any number of user devices 108 linked to the particular user or patient. In this regard, a user device 108 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. For the example described here, the medication delivery system 102 and the at least one user device 108 are owned by, operated by, or otherwise linked to a user/patient. Any given user device 108 can host, run, or otherwise execute the patient care application 110. In certain embodiments, for example, the user device 108 is implemented as a smartphone with the patient care application 110 installed thereon. In accordance with another example, the patient care application 110 is implemented in the form of a website or webpage, e.g., a website of a healthcare provider, a website of the manufacturer, supplier, or retailer of the medication delivery system 102, or a website of the manufacturer, supplier, or retailer of the analyte sensor 112. In accordance with another example, the medication delivery system 102 executes the patient care application 110 as a native function.

In certain embodiments, at least some of the features or output of the gesture-based physical behavior detection system 104 and/or the ancillary system(s) 106 can be used to influence features, functions, and/or therapy-related operations of the medication delivery system 102. As described in more detail below, the gesture-based physical behavior detection system 104 includes one or more sensors, detectors, measurement devices, and/or readers to automatically detect certain user gestures that correlate to user activities or events (e.g., socializing, eating, sleeping, exercising, or watching television). The gesture-based physical behavior detection system 104 may communicate gesture data to the medication delivery system 102, the user device 108, and/or the data processing system 116 for processing in an appropriate manner for use in regulating or controlling certain functions of the medication delivery system 102. For example, the gesture data may be communicated to a user device 108, such that the user device 108 can process the gesture data and inform the user or the medication delivery system 102 as needed (e.g., remotely regulate or control certain functions of the medication delivery system 102). As another example, the gesture-based physical behavior detection system 104 may communicate the gesture data to one or more cloud computing systems or servers (such as a remote data processing system 116) for appropriate processing and handling in the manner described herein.

Similarly, an ancillary system 106 may include one or more sensors, detectors, measurement devices, and/or readers that obtain ancillary user status data that correlates to events or activities by a user. In certain embodiments, an ancillary system 106 may include, cooperate with, or be realized as any of the following, without limitation: a heartrate monitor linked to the user; a blood pressure monitor linked to the user; a respiratory rate monitor linked to the user; a vital signs monitor linked to the user; a microphone; a thermometer (for the user's body temperature and/or the environmental temperature); a sweat detector linked to the user; an activity tracker linked to the user; a global positioning system (GPS); a clock, calendar, or appointment application linked to the user; a pedometer linked to the user; or the like. An ancillary system 106 may be configured and operated to communicate its output (user status data) to one or more components of the system 100 for analysis, processing, and handling in the manner described herein. In certain embodiments, user status data obtained from one or more ancillary systems 106 supplements the gesture data obtained from the gesture-based physical behavior detection system 104, such that user habits, physical behavior, and activity events are accurately and reliably detected.

In certain embodiments, the gesture-based physical behavior detection system 104 and the medication delivery system 102 are implemented as physically distinct and separate components, as depicted in FIG. 1. In such embodiments, the gesture-based physical behavior detection system 104 is external to the medication delivery system 102 and is realized as an ancillary component, relative to the medication delivery system 102. In accordance with alternative embodiments, however, the medication delivery system 102 and the gesture-based physical behavior detection system 104 can be combined into a single hardware component or provided as a set of attached hardware devices. For example, the medication delivery system 102 may include the gesture-based physical behavior detection system 104 or integrate the functionality of the detection system 104. Similarly, the analyte sensor 112 can be incorporated with the medication delivery system 102 or the gesture-based physical behavior detection system 104. These and other arrangements, deployments, and topologies of the system 100 are contemplated by this disclosure.

The at least one patient history and outcomes database 114 includes historical data related to the user's physical condition, physiological response to the medication regulated by the medication delivery system 102, activity patterns or related information, eating patterns and habits, work habits, and the like. In accordance with embodiments where the medication delivery system 102 is an insulin infusion device and the analyte sensor 112 is a glucose meter, sensor, or monitor, the database 114 can maintain any of the following, without limitation: historical glucose data and corresponding date/time stamp information; insulin delivery and dosage information; user-entered stress markers or indicators; gesture data (provided by the gesture-based physical behavior detection system 104) and corresponding date/time stamp information; ancillary user status data (provided by one or more ancillary systems 106) and corresponding date/time stamp data; diet or food intake history for the user; and any other information that may be generated by or used by the system 100 for purposes of controlling the operation of the medication delivery system 102. In certain embodiments, the at least one patient history and outcomes database 114 can receive and maintain training data that is utilized to train, configure, and initialize the system 100 based on historical user behavior, physiological state, operation of the medication delivery system 102, and user-identified activity events.

A patient history and outcomes database 114 may reside at a user device 108, at the medication delivery system 102, at a data processing system 116, or at any network-accessible location (e.g., a cloud-based database or server system). In certain embodiments, a patient history and outcomes database 114 may be included with the patient care application 110. The patient history and outcomes database 114 enables the system 100 to generate recommendations, warnings, and guidance for the user and/or to regulate the manner in which the medication delivery system 102 functions to administer therapy to the user, based on detected user activity.

Figure 6:
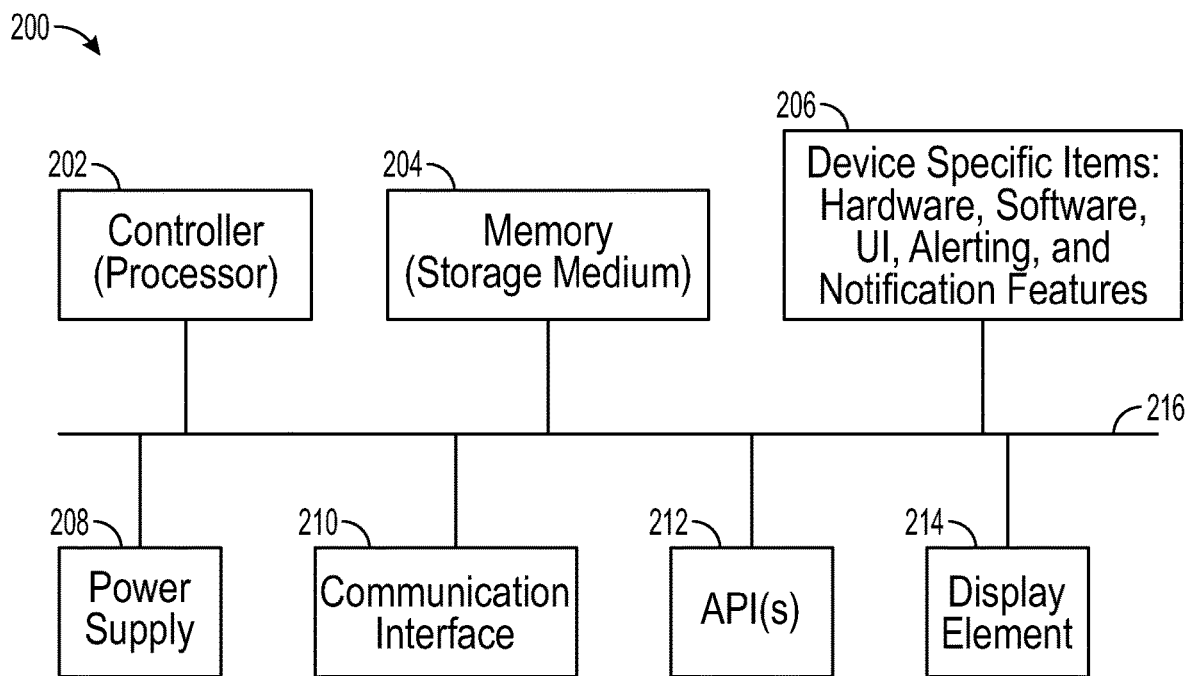
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication device 210; at least one application programming interface (API) 212; and a display element 214. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200. In practice, the elements of the device 200 may be coupled together via at least one bus or any suitable interconnection architecture 216.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively, or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 6.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 214. The display element 214 and/or the device-specific items 206 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication device 210 facilitates data communication between the device 200 and other components as needed during the operation of the device 200. In the context of this description, the communication device 210 can be employed to transmit or stream device-related control data, patient-related user status (e.g., gesture data or status data), device-related status or operational data, sensor data, calibration data, and the like. It should be appreciated that the particular configuration and functionality of the communication device 210 can vary depending on the hardware platform and specific implementation of the device 200. In practice, an embodiment of the device 200 may support wireless data communication and/or wired data communication, using various data communication protocols. For example, the communication device 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB.

Moreover, the communication device 210 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 212 supports communication and interactions between software applications and logical components that are associated with operation of the device 200. For example, one or more APIs 212 may be configured to facilitate compatible communication and cooperation with the patient care application 110, and to facilitate receipt and processing of data from sources external to the device 200 (e.g., databases or remote devices and systems).

The display element 214 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 214 may also be utilized for the display of other information during the operation of the device 200, as is well understood. Notably, the specific configuration, operating characteristics, size, resolution, and functionality of the display element 214 can vary depending upon the implementation of the device 200.

Figure 7:
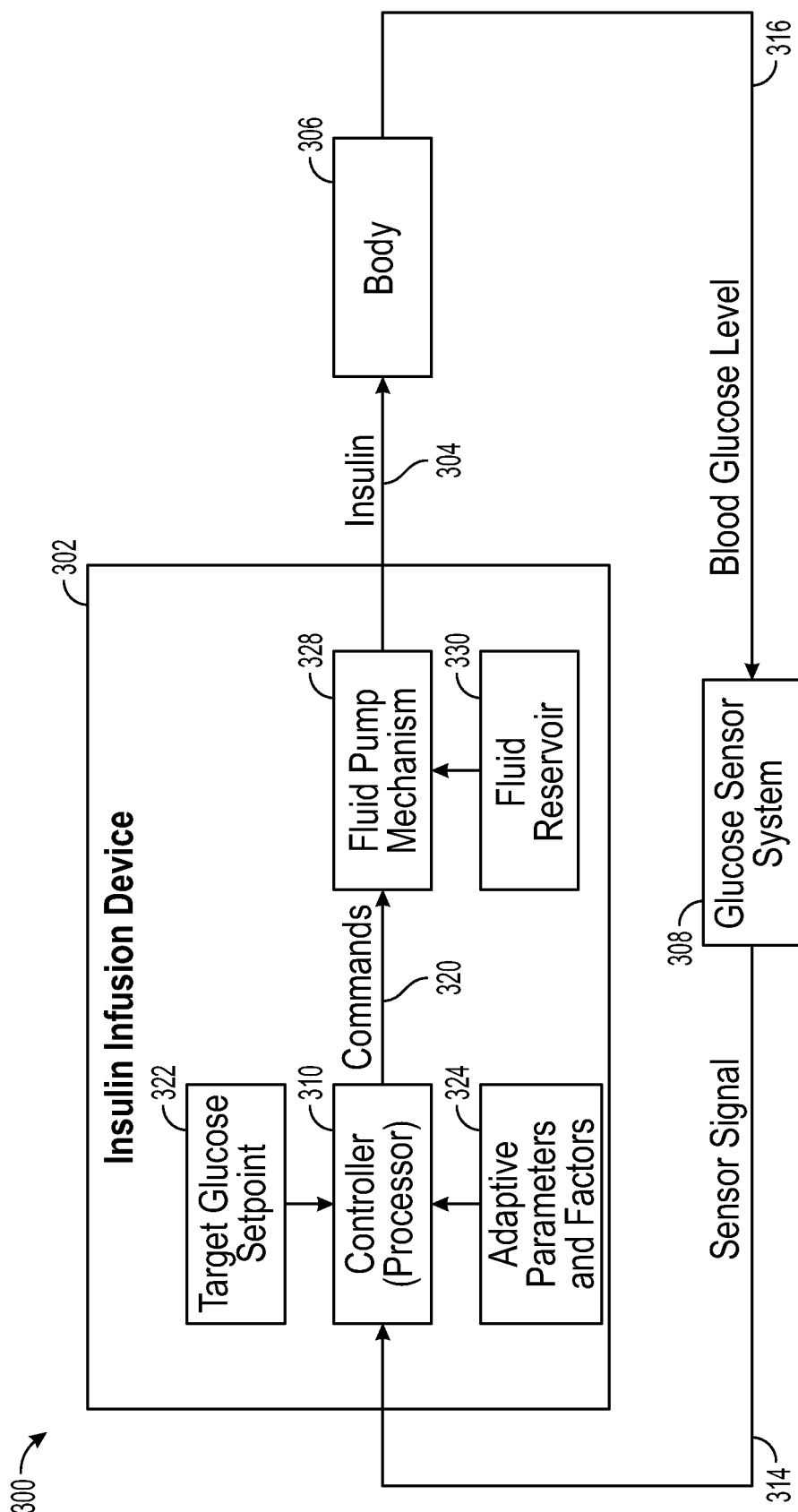
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 300 arranged in accordance with certain embodiments. The system 300 depicted in FIG. 7 functions to regulate the rate of fluid infusion into a body of a user based on feedback from an analyte concentration measurement taken from the body. In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human β-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 112 shown in FIG. 1); and at least one controller 310, which may be incorporated in the insulin infusion device 302 as shown in FIG. 7. The glucose sensor system 308 generates a sensor signal 314 representative of blood glucose levels 316 in the body 306, and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a target glucose setpoint value 322 that is maintained and regulated by the insulin infusion device 302. Moreover, the commands 320 (and, therefore, the delivery of insulin 304) can be influenced by any number of adaptive parameters and factors 324. The adaptive parameters and factors 324 may be associated with or used by: a therapy control algorithm of the insulin infusion device 302; a digital twin model of the patient, which can be used to recommend manual insulin dosages; a meal prediction algorithm; a user glucose prediction algorithm; or the like.

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 6, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, the adaptive parameters and factors 324, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 6, the insulin infusion device 302 may be implemented as a computer-based or processor-based components having the described configuration and features, including the display element 214 or other device-specific items 206 as described above.

The controller 310 is configured and programmed to regulate the operation of the fluid pump mechanism 328 and other functions of the insulin infusion device 302. The controller 310 controls the fluid pump mechanism 328 to deliver the fluid medication (e.g., insulin) from the fluid reservoir 330 to the body 306. As mentioned above, the controller 310 can be housed in the infusion device housing, wherein the infusion communication system is an electrical trace or a wire that carries the commands 320 from the controller 310 to the fluid pump mechanism 328. In alternative embodiments, the controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

Referring again to FIG. 1, the gesture-based physical behavior detection system 104 employs at least one sensor to obtain corresponding user-specific sensor data. The obtained user-specific sensor data is processed or analyzed by the gesture-based physical behavior detection system 104 and/or by another suitably configured device or component of the system 100 to determine whether the user's current behavior reflects a significant or measurable change in activity. The obtained user-specific sensor data may also be processed or analyzed to obtain certain activity-related parameters, characteristics, and/or metadata for the user. For example, the obtained user-specific sensor data may identify, include, or indicate any or all of the following, without limitation: timestamp data corresponding to the occurrence of detected events; a type, category, or classification of the detected physical behavior or activity; location data; user posture or position information; etc.

The gesture-based physical behavior detection system 104 may include, cooperate with, or be realized as a motion-based physical behavior detection system, an activity-based physical behavior detection system, an image or video based activity detection system, or the like. In certain embodiments, the detection system 104 may be realized as a unitary "self-contained" wearable system that communicates with one or more other components of the system 100. For example, the detection system 104 can be implemented with at least one wearable device such as an activity monitor device, a smart watch device, a smart bracelet or wristband device, or the like. In some embodiments, the detection system 104 may be realized as at least one portable or wearable device that includes or communicates with one or more external or ancillary sensor devices, units, or components. For example, the detection system 104 can be implemented with a wearable or portable smart device that is linked with one or more external sensors worn or carried by the user. These and other possible deployments of the detection system 104 are contemplated by this disclosure. In this regard, United States patent publication number US 2020/0135320 and United States patent publication number US 2020/0289373 disclose gesture-based physical behavior detection systems that are suitable for use as the detection system 104; the entire content of these United States patent documents is incorporated by reference herein.

Figure 8:
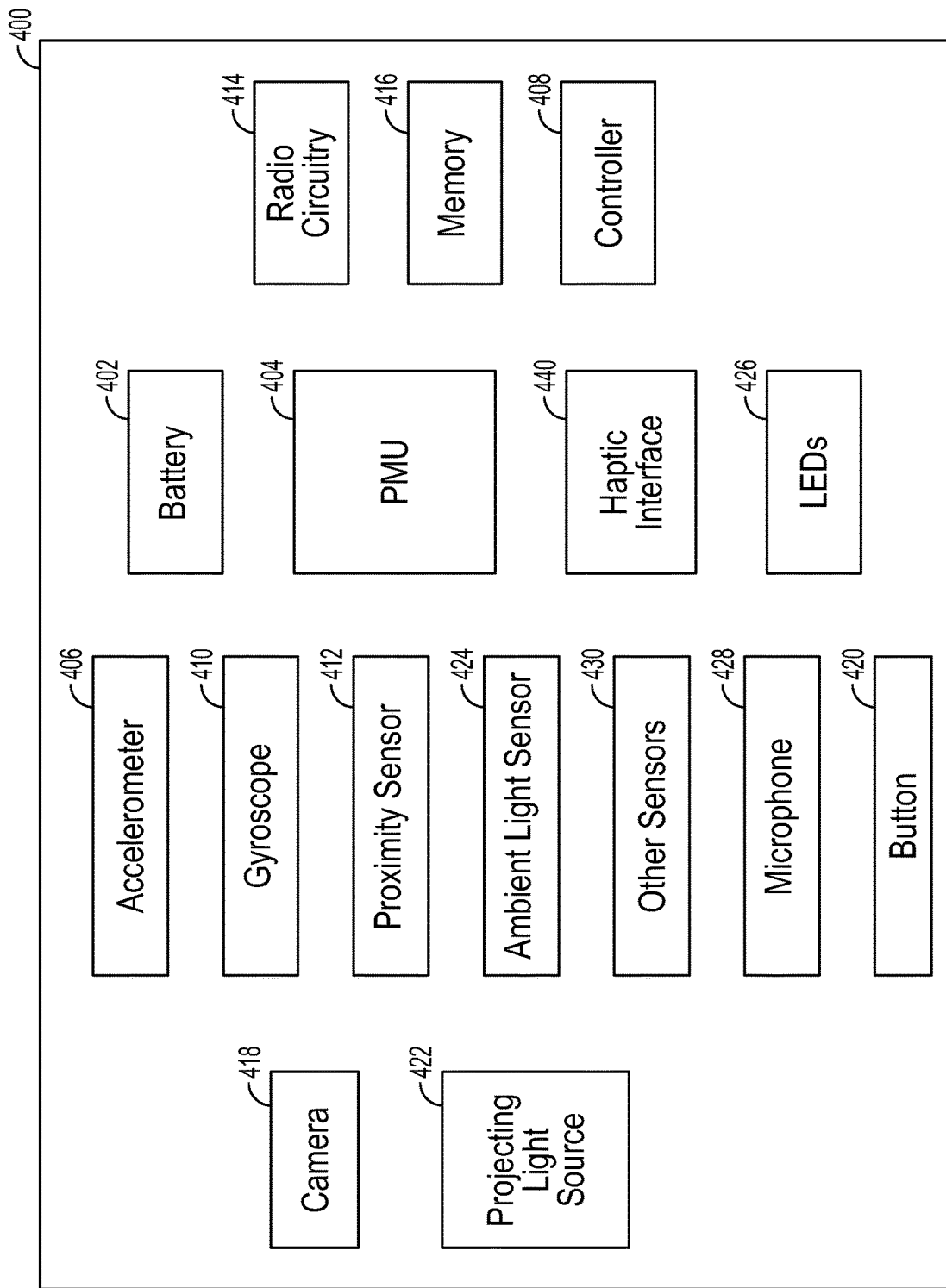
FIG. 8 is a block diagram representation of a gesture-based physical behavior detection system arranged in accordance with certain embodiments.

FIG. 8 is a block diagram representation of a gesture-based physical behavior detection system 400 arranged in accordance with certain embodiments. The system 400 is suitable for use with the system 100 shown FIG. 1. In certain embodiments, the system 400 is deployed as a wearable electronic device in the form factor of a bracelet or wristband that is worn around the wrist or arm of a user's dominant hand. The system 400 may optionally be implemented using a modular design, wherein individual modules include one or more subsets of the disclosed components and overall functionality. The user may choose to add specific modules based on personal preferences and requirements.

The system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the system 400 are switched off to conserve power. Only circuitry and components that are required to detect or help predict the start of a behavior event of interest may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the system 400 to a destination device may be placed in a lower power mode. For example, radio circuitry 414 could be disabled. Similarly, the circuitry required to transfer data from the system 400 may be placed in a lower power mode. For example, the radio circuitry 414 could be disabled until a possible or likely start of a behavior event has been determined. Alternatively, it may remain enabled but in a low power state to maintain the connection between the system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the system 400 has been removed from the wrist or hand, detection that the system 400 is being charged, or the like. Metadata may be generated and collected by the system 400. Alternatively, metadata may be collected by another device that is external to the system 400 and is configured to directly or indirectly exchange information with the system 400. It is also possible that some metadata is generated and collected by the system 400, while other metadata is generated and collected by a device that is external to the system 400. In case some or all of the metadata is generated and collected external to the system 400, the system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user beginning to work, jog, or eat, is likely. Metadata used to make this determination may, among other things, include one or more of the following: time of the day; location; ambient light levels; proximity sensing; historical user behavior patterns. Some or all of the metadata may be collected by the system 400 or by an ancillary device that cooperates or communicates with the system 400, as mentioned above.

User status data used to track certain aspects of a user's behavior may be stored locally inside memory 416 of the system 400 and processed locally using the controller 408 of the system 400. User status data may also be transferred to the medication delivery system 102, the patient care application 110, and/or one or more of the database 114 mentioned above with reference to FIG. 1 (such that the user status data can be processed, analyzed, or otherwise utilized by the applications or components that receive the user status data). It is also possible that some of the processing and analysis are performed locally by the system 400, while further processing and analysis are performed by one or more other components of the system 100.

The detection of the start of a behavior event, such as the start of a work activity, may trigger the power up and/or activation of additional sensors and circuitry, such as a camera 418. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 418 only gets powered up or activated upon explicit user intervention such as, for example, pushing and holding a button 420. Releasing the button 420 may turn off the camera 418 to conserve power.

When the camera 418 is powered up, a projecting light source 422 may also be enabled to provide visual feedback to the user about the area that is within view of the camera or to otherwise illuminate the field of view. Alternatively, the projecting light source 422 may only be activated sometime after the camera 418 has been activated. In certain cases, additional conditions may need to be met before the projecting light source 422 is activated. Such conditions may include: the determination that the projecting light source 422 is likely aiming in the direction of the object of interest; the determination that the system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. In certain embodiments, audio captured by the microphone 428 can be processed to assist in the determination of whether the user is eating, drinking, commuting, exercising, working, or resting. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the system 400 may include or cooperate with any number of other sensors 430 as appropriate for the particular embodiment. For example, and without limitation, the system 400 may include or cooperate with any or all of the following: a heartrate monitor; a physiological characteristic or analyte sensor; a continuous glucose monitor; a GPS receiver; and any other sensor, monitor, or detector mentioned elsewhere herein. The system 400 obtains user status data from one or more of its sensors, detectors, and sources, wherein the user status data indicates a stressful activity of the user. The user status data can be analyzed and processed by the system 400 (and/or by one or more other components of the system 100) to determine whether the user's current behavior is consistent with normally expected behavior or activity. In certain embodiments, the system 400 and/or an ancillary system 106 or device determines the user's activity and related behavior primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the system 400.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs (such as the output from one or more ancillary systems 106) to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating a meal, going to bed, working out) has occurred, whether an event is ongoing, whether an event has ended, or the like. Although this description mentions meal detection, the gesture-based physical behavior detection system 400 may be suitably configured to monitor other types of physical behavior or activities. Such activities include, without limitation: reading; sleeping; smoking; getting dressed; driving; walking; commuting; working; exercising; turning down a bed; making a bed; brushing teeth; combing hair; talking on the phone; inhaling or injecting a medication; and activities related to hand hygiene or personal hygiene.

Figure 9:
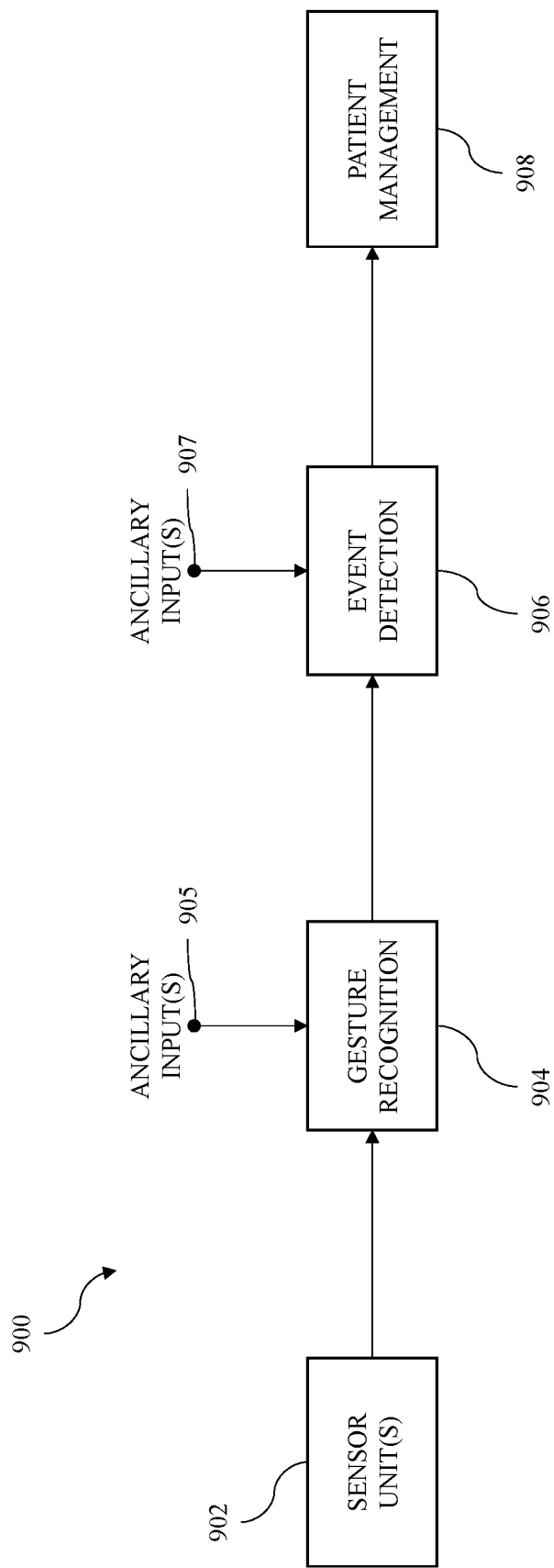
FIG. 9 is a block diagram representation of an embodiment of a gesture-informed patient management system in accordance with certain embodiments.

FIG. 9 is a simplified block diagram representation of an embodiment of a gesture-informed patient management system 900. The depicted patient management system 90 includes, without limitation, one or more sensor units 902, a gesture recognition unit 904, an event detection unit 906, and a patient management unit 908.

The sensor unit(s) 902 generally represent the sensor(s) embedded in, integrated with, or otherwise associated with one or more portable or wearable devices associated with a patient, such as, for example, an activity tracker, a smart watch, a wristband, a ring, a mobile phone, or a portable electronic medical device (e.g., a continuous glucose monitoring device, an infusion device, an injection pen, and/or the like). For example, in one or more exemplary embodiments, the sensor unit(s) 902 include an accelerometer (e.g., accelerometer 406) and a gyroscope (e.g., gyroscope 412) associated with a smart watch. That said, it should be appreciated the patient management system 900 is not limited to any particular type, configuration, or number of sensor unit(s) 902, and in practice, the sensor unit(s) 902 may include one or more of the following sensing arrangements: accelerometers, gyroscopes, magnetometers, image sensors, cameras, optical sensors, proximity sensors, pressure sensors, odor sensors, gas sensors, Global Positioning Systems (GPS) receivers, microphones, galvanic skin response sensors, thermometers, ambient light sensors, UV sensors, electrodes for electromyographic ("EMG") potential detection, bio-impedance sensors, spectrometers, glucose sensors, heart rate sensors, pulse sensors, touchscreen or capacitive sensors. In this regard, the output of the sensor unit(s) 902 may include any sort of motion data, location data, physiological data (e.g., temperature, heart rate, pulse, galvanic skin response, blood or body chemistry, and/or the like), or other sensor data depending on the sensor type. The output of the sensor unit(s) 902 may be communicated to the gesture recognition unit 904 wirelessly or via wires, in analog or digital form, directly or indirectly (e.g., intermediated by gating and/or clocking circuits, analog-to-digital converters, and/or the like).

The gesture recognition unit 904 generally represents a software application or component of the patient management system 900 that receives the sensor data signals from the sensor unit(s) 902 and analyzes the received sensor data to detect or otherwise identify gestures performed by the patient based on the received sensor data. In this regard, a gesture generally represents a discrete set of one or more physical movements having associated spatial and/or temporal characteristics that are distinguishable from other gestures. For example, as described in United States Patent Publication Number 2020/0289373, the gesture recognition unit 904 may utilize machine learning or other artificial techniques to map different subsets of sensor data within a stream of received sensor data to different gesture features, which, in turn, are then analyzed to classify or otherwise resolve the different subsets of the sensor data and corresponding gesture features into a particular combination or sequence of gestures performed by the patient. In one or more embodiments, the gesture recognition unit 904 fuses or otherwise combines concurrent or otherwise temporally-associated accelerometer data and gyroscope data to obtain an orientation vector, with the concurrent or temporally-associated combinations of accelerometer data, gyroscope data, and fused orientation vectors being input to a feature generator, which, in turn, generates a corresponding stream of gesture features, which, in turn are input to the gesture recognition model which classifies or otherwise resolves the stream of gesture features into corresponding gestures. In exemplary embodiments, the gesture recognition unit 904 also associates or otherwise assigns a confidence metric to each gesture based on the gesture features. In this regard, for a given stream of sensor data received by the gesture recognition unit 904, the gesture recognition unit 904 outputs a corresponding stream of gestures and associated confidence levels.

In some embodiments, the gesture recognition unit 904 receives one or more ancillary inputs 905 which may influence the gesture detection or the confidence or probability assigned to detected gestures. For example, the ancillary input 905 may include operational contextual data, such as, the current time of day, the current day of the week, the current month of the year, the current location of the patient, and/or the like, along with other patient-specific data such as historical gesture data associated with the patient, a patient profile associated with the patient or other patient-specific personalization that may be utilized by the gesture recognition unit 904 to influence manner in which particular gesture features are mapped to a gesture for the particular patient. In this regard, statistical analysis of the historical gesture data and potentially other patient-specific data may be utilized to determine or otherwise assign probabilities of a specific gesture occurring based on the current operational context. It should be noted that there are any number of different types of ancillary input data (e.g., from at least one ancillary system 106 from FIG. 1) that may be correlative to the occurrence or non-occurrence of a particular gesture, and the subject matter described herein is not limited to any particular type or combination of ancillary inputs 905 that may be utilized by the gesture recognition unit 904.

In one or more embodiments, the executable code or programming instructions corresponding to the gesture recognition unit 904 is stored or otherwise maintained in a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by a processor or other processing system. For example, in one or more exemplary embodiments, the computer-executable programming instructions corresponding to the gesture recognition unit 904 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the gesture recognition unit 904 at the wearable electronic device. In this regard, in some embodiments, the wearable electronic device may transmit or otherwise provide signals or data indicating a stream of detected gestures and associated confidence levels to another device for further processing and/or analysis. That said, in other embodiments, the gesture recognition unit 904 may be implemented at or on a patient's mobile phone or other portable electronic device (e.g., user device 108) that receives sensor data signals from the sensor unit(s) 902 via a wireless network, or be implemented at or on a cloud computing system or remote server that receives the sensor data signals from the sensor unit(s) 902 via the Internet, a cellular network, or the like.

Still referring to FIG. 9, the event detection unit 906 generally represents a software application or component of the patient management system 900 that receives the detected gestures and confidence levels from the from the gesture recognition unit 904 and analyzes the received gesture data to detect or otherwise identify events or activities performed by the patient based on the received gesture data. For example, as described in United States Patent Publication Number 2020/0289373, the event detection unit 906 may utilize machine learning or other artificial techniques to map a stream of detected gestures and associated confidence levels into a particular event or activity being performed by the patient based on the type of gestures detected, the sequence of detected gestures, the temporal relationship between gestures and/or the confidence metrics assigned to the detected gestures. In this manner, the event detection unit 906 may map lower-level gestures into a higher-level physical behavior while filtering or otherwise deemphasizing false positives or spurious gestures. Thus, for a given stream of detected gestures received by the event detection unit 906, the event detection unit 906 outputs an indication of a detected event or activity by the patient and an associated confidence or probability metric for the event. For example, for a sequence of detected food intake gestures may be mapped or otherwise recognized as a food intake event having a particular start time, pace, duration, and/or the like with an assigned level of confidence or probability influenced by the confidence associated with the detected food intake gestures and potentially other factors.

In a similar manner as described above for the gesture recognition unit 904, the event detection unit 906 may receive ancillary input 907 which may influence the event detection or the confidence or probability assigned to detected events. For example, the ancillary input 907 may include event log data associated with the patient that maintains data pertaining to historical events or activities by the patient (e.g., meals, exercise, sleep, boluses, glucose excursion events, and/or the like), with statistical analysis of the historical event log data and potentially other patient-specific data being utilized to determine or otherwise assign probabilities of a specific event occurring based on the current operational context. In this regard, if the patient habitually engages in meals at or around a certain time of day, food intake gestures occurring at that time of day consistent with the patient's historical behavior may be more likely to be mapped to a meal event or other food intake event, or the detected meal event or food intake event may be assigned a higher probability or confidence value based on the correlation and consistency with the patient's historical behavior. Again, it should be noted that there are any number of different types of ancillary input data that may be correlative to the occurrence or non-occurrence of a particular event, and the subject matter described herein is not limited to any particular type or combination of ancillary inputs 907 that may be utilized by the event detection unit 906.

In one or more embodiments, the executable code or programming instructions corresponding to the event detection unit 906 is stored or otherwise maintained in a data storage element or memory, including any sort of short or long term storage media or other non-transitory computer-readable medium, which is capable of storing programming instructions for execution by a processor or other processing system. For example, in one or more exemplary embodiments, the computer-executable programming instructions corresponding to the event detection unit 906 are stored in a data storage element (e.g., memory 416) of a wearable electronic device including the sensor unit(s) 902, and, when read and executed by a processing system (e.g., controller 408) of the wearable electronic device, the instructions cause the wearable electronic device to generate the event detection unit 906 at the wearable electronic device. In this regard, in some embodiments, the wearable electronic device may transmit or otherwise provide signals or data indicating a stream of detected events and associated confidence or probability levels to another device for further processing and/or analysis. That said, in other embodiments, the event detection unit 906 may be implemented at or on a patient's mobile phone or other portable electronic device (e.g., user device 108) or on a cloud computing system or remote server that receives gesture data signals from the gesture recognition unit 904 implemented at another device via a network.

Still referring to FIG. 9, the patient management unit 908 generally represents a software application or component of the patient management system 900 that receives the detected event data from the event detection unit 906 and automatically initiates or otherwise performs one or more actions with respect to management of the patient's physiological condition. In some embodiments, the patient management unit 908 is configurable to support one or more autonomous operating modes for an infusion device, a smart pen, or other fluid delivery device, where the patient management unit 908 calculates or otherwise determines dosage commands for operating an actuation arrangement to deliver fluid to the patient. For example, in a closed-loop operating mode, the patient management unit 908 may determine a dosage command based at least in part on a current glucose measurement value for the patient in a manner that is influenced by an event detected by the event detection unit 906. In some embodiments, the patient management unit 908 is configurable to generate or otherwise provide user notifications or alerts via a user interface element based at least in part on a detected event. In this regard, the patient management unit 908 may utilize patient-specific settings, preferences, or other notification criteria to automatically generate user notifications in a manner that is influenced by the detected event and potentially other factors (e.g., the patient's current or recent sensor glucose measurement values). For example, in one or more embodiments, for a patient on a MDI therapy regimen where the medication delivery system 102 includes a smart pen or other injection device, the patient management unit 908 may utilize patient-specific settings, preferences, or other notification criteria to automatically generate user notifications that indicate recommended bolus amounts, a recommended time (or window of time) for when a bolus should be delivered, and/or the like to assist the patient in administering an appropriate bolus that is responsive to a gestured event and reflects the current operational context.

In one or more embodiments, the executable code or programming instructions corresponding to the patient management unit 908 is stored or otherwise maintained at one of the patient's associated devices (e.g., the patient's mobile phone, the patient's infusion device or other fluid delivery device, or the like) or at a cloud computing system or remote server. For example, the patient management unit 908 executing on the patient's phone may receive or otherwise obtain signals or data indicating detected gestures and/or events from the patient's smart watch or other wearable device, analyze the received data, and transmit or otherwise provide dosage commands or signals influenced by the detected gestured-based events to the patient's infusion device (e.g., via a wireless network) to automatically operate the infusion device to deliver insulin or another fluid or medicament to account for the detected event(s), or the patient management unit 908 may generate GUI displays or other user notifications influenced by the detected event(s) at the mobile device. That said, in other embodiments, when the patient management unit 908 is implemented at a remote server or other cloud computing system, the patient management unit 908 may transmit or otherwise provide dosage commands or signals to a device associated with the patient via a network. In yet other embodiments, the patient management unit 908 may be implemented at the patient's medical device and receive detected event data from the patient's mobile device, the patient's wearable device, or a remote server or other cloud computing system. In this regard, depending on the embodiment, the various units 904, 906, 908 may be distributed across one or more different devices 102, 104, 106, 108, 116 in a system 100 and the subject matter described herein is not limited to any particular implementation. For example, the event detection unit 906 and the patient management unit 908 may be implemented by the patient care application 110 at the user device 108 receiving the detected gesture data stream signals output by the gesture detection system 104 from the gesture detection system 104 via a wireless network.

Figure 10:
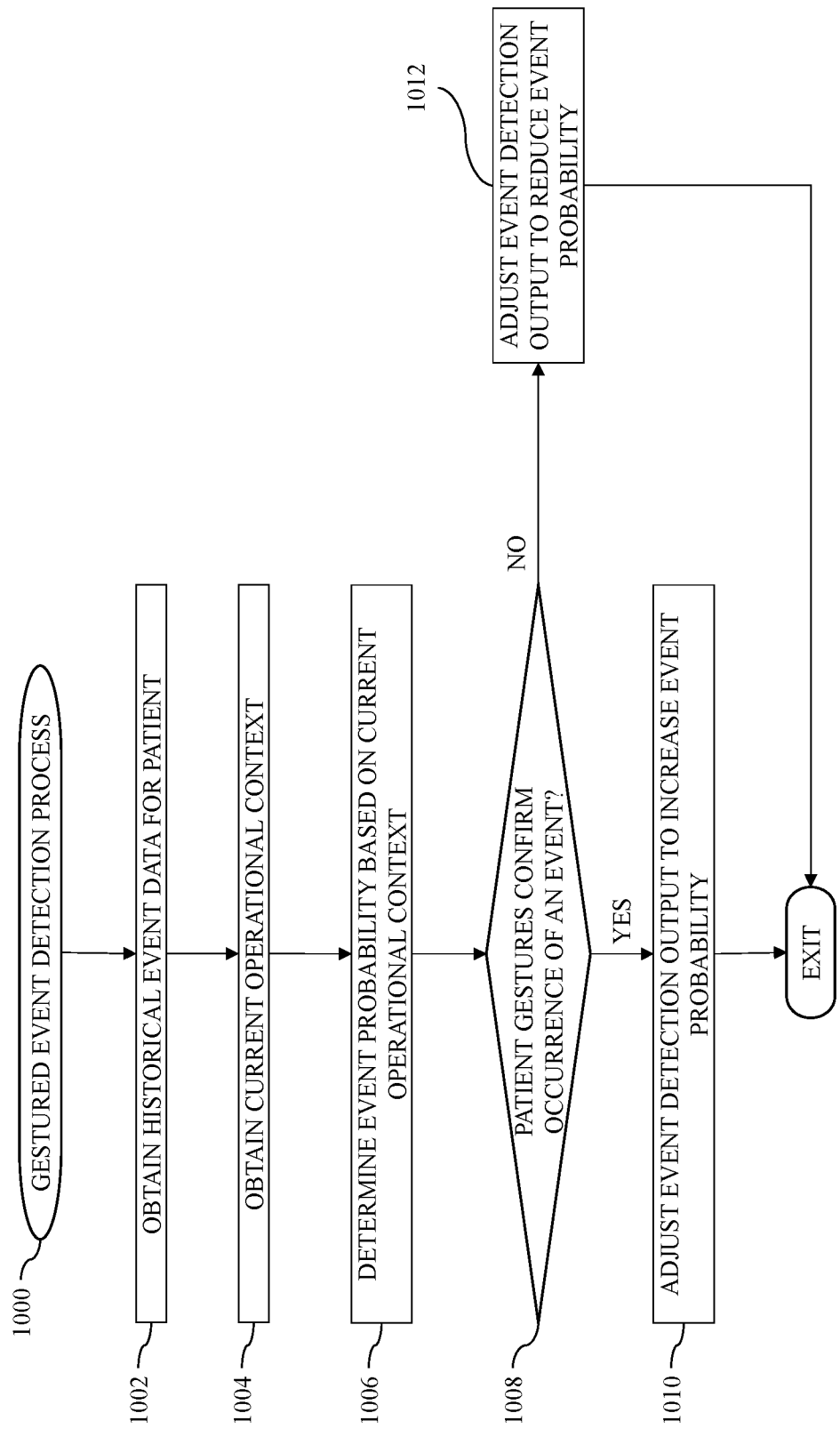
FIG. 10 is a flow diagram of an exemplary gestured event detection process in accordance with one or more exemplary embodiments.

FIG. 10 depicts an exemplary gestured event detection process 1000 suitable for implementation by a patient management system (e.g., system 100, device 200, system 300, patient management system 900) to predict occurrence of events and provide corresponding notifications, recommendations, or other responsive actions. The various tasks performed in connection with the gestured event detection process 1000 may be performed by hardware, firmware, software executed by processing circuitry, or any combination thereof. For illustrative purposes, the following description refers to elements mentioned above in connection with FIGS. 1-9. It should be appreciated that the gestured event detection process 1000 may include any number of additional or alternative tasks, the tasks need not be performed in the illustrated order and/or the tasks may be performed concurrently, and/or the gestured event detection process 1000 may be incorporated into a more comprehensive procedure or process having additional functionality not described in detail herein. Moreover, one or more of the tasks shown and described in the context of FIG. 10 could be omitted from a practical embodiment of the gestured event detection process 1000 as long as the intended overall functionality remains intact.

The gestured event detection process 1000 may be performed to inform, influence, or otherwise augment the detection of events in response to detected gestures in a manner that accounts for the current operational context, that is, the current time of day, the current day of the week, the current month of the year, the current geographic location, the current environmental conditions, and/or the current values or states of other contextual measurement data that characterizes, quantifies, or otherwise indicates the contemporaneous or concurrent operating context. For example, the gestured event detection process 1000 may be performed to automatically adjust closed-loop control information or other fluid delivery parameters or recommendations for an infusion device or an injection device (e.g., bolus amount, total daily dose, therapy schedule) to account for the detected event in a manner that reflects the probable or likely characteristics of the event given the current operational context and/or the relative probability or likelihood of occurrence of the event given the current operational context. Thus, historical data for a given patient may be utilized in connection with gestures detected by a wearable device to improve accuracy or reliability based on consistency (or inconsistency) with prior behavior by the patient (or similar patients or users) given the same or substantially similar operational contexts in the past.

The gestured event detection process 1000 begins by receiving or otherwise obtaining historical event data for the patient, receiving or otherwise obtaining information characterizing the current operational context, and calculating or otherwise determining event probabilities based at least in part on the correlation between the current operational context and the historical operational context associated with past events (tasks 1002, 1004, 1006). For example, the event detection unit 906 may retrieve or otherwise obtain the historical event data associated with the patient from a database (e.g., database 114 via ancillary input 907) and analyze the historical event data to identify previous events logged, entered, or otherwise input by the patient or other user. Based on the timestamps and other contextual data associated with those previous events (e.g., geolocation data, and/or the like), the event detection unit 906 may calculate or otherwise determine the probability of the patient experiencing or engaging in a particular type of event at a particular time or within a particular window of time given the current operational context (e.g., the current time of day, the current day of the week, current geographic location of the infusion device, etc.). For example, probability of event occurrence given the current operational context can be determined by dividing the number of events associated with the current operational context (or a subset of contextual variables) by the total number of instances when the current operational context (or a subset of contextual variables) is observed within the patient's historical data. Additionally, the probable characteristics or attributes associated with the event occurrence may be determined based on prior events matching the current operational context. For example, historical meal data for the patient may be analyzed to identify the probability of a meal occurring based on prior meal events matching the current operational context and the probable characteristics or attributes of the meal based on the prior meal events that match the current operational context (e.g., by averaging attributes associated with those prior meals). Thus, for a given operational context, the event detection unit 906 may determine the probability of occurrence for different types of events along with probable attributes for the different events based on the historical patient data received via ancillary input 907.

In one or more embodiments, the event detection unit 906 provides indicia of the predicted event(s) for the current operational context to the patient management unit 908 for dynamically and automatically adjusting operation of a medical device to account for the predicted occurrence of an event. For example, the event detection unit 906 may output a probability of occurrence of a meal event for the current operational context to the patient management unit 908 along with indicia of one or more probable attribute(s) for the meal event (e.g., meal time, duration, carbohydrate count, portion size(s), and/or the like). Based on the received meal event probability and probable meal attributes, the patient management unit 908 automatically determine commands for adjusting delivery of insulin by an infusion device to account for the meal event. As another example, the event detection unit 906 output a probability of occurrence of an exercise event for the current operational context to the patient management unit 908 along with indicia of one or more probable attribute(s) for the exercise event (e.g., a probable exercise duration, a probable exercise intensity, and/or the like) to the patient management unit 908 for automatically adjusting insulin delivery and/or therapy. In this manner, the patient management unit 908 may automatically configure a patient's medical device to regulate, control, or otherwise influence the patient's physiological condition to account for the probable occurrence of an event predicted for the current operational context based on correlations between the patient's historical event data and the current operational context.

Still referring to FIG. 10, the gestured event detection process 1000 detects or otherwise identifies one or more gestures by the patient indicative of an event, and in response to detecting a gestured event that confirms occurrence of a predicted event for the current operational context, automatically adjusts or otherwise augments the event detection output to increasingly account for the gestured event (tasks 1008, 1010). On the other hand, in some embodiments, in response to the absence of the predicted event, the gestured event detection process 1000 automatically adjusts or otherwise augments the event detection output to deemphasize an event occurrence predicted based on the current operational context (task 1012). In this regard, depending on whether the gesture data is consistent or inconsistent with the occurrence of an event predicted based on the current operational context, the output(s) of the event detection unit 906 may be adjusted in a corresponding manner to increase or decrease the probability associated with the event, and thereby improve the accuracy or reliability of the event data provided to the patient management unit 908, which, in turn, may automatically reconfigure the patient's medical device to reflect the detected occurrence or absence of the predicted event.

For example, when the detected gesture data stream received by the event detection unit 906 from the gesture recognition unit 904 indicates occurrence of a food intake event or other meal event, the event detection unit 906 may automatically increase the probability or confidence value associated with the occurrence of a meal event that was previously predicted based on the current operational context. In response to an increased probability of occurrence of a meal event or in response to the probability of occurrence being above a particular threshold for particular meal event, the patient management unit 908 may automatically command or otherwise adjust an infusion device or other fluid delivery device associated with the patient to increase insulin therapy or otherwise respond more aggressively to increases in the patient's sensed glucose measurement values. In a similar manner, when the detected gesture data stream indicates occurrence of an exercise event (e.g., when the confidence value or probability of occurrence of the exercise event is above a particular threshold that type of meal event), the event detection unit 906 may increase the probability or confidence value associated with the occurrence of an exercise event previously predicted based on the current operational context to cause the patient management unit 908 automatically reconfigure the patient's medical device in a corresponding manner (e.g., by reducing insulin delivery and/or recommended therapy). The detected gesture data stream may also be utilized by the event detection unit 906 to refine, augment or otherwise adjust the attributes for the detected event, such as, for example, the event duration, the size or intensity of the event, and/or the like, which, in turn, may similarly influence the manner in which the patient management unit 908 adjusts operation of the patient's medical device to account for the refined prediction of the event attributes.

Conversely, when the current operational context indicates the likely occurrence of an event for the patient but the output of the gesture recognition unit 904 does not include or otherwise indicate any gestures for that event (or includes contradictory gestures), the event detection unit 906 may automatically decrease the probability or confidence value associated with a meal event that would otherwise be predicted based on the current operational context. For example, when the current operational context indicates the likely occurrence of a meal event for the patient but the output of the gesture recognition unit 904 does not include or otherwise indicate any food intake gestures, the event detection unit 906 may automatically decrease the probability or confidence value associated with a meal event that would otherwise be predicted based on the current operational context. In a similar manner, the probability or confidence value associated with an exercise event that would otherwise be predicted based on the current operational context may be decreased when the detected gesture data stream indicates the patient is eating, inactive, and/or the like. In some embodiments, patient management unit 908 may forego commanding or otherwise adjusting an infusion device or other fluid delivery device when the probability of occurrence of a particular type of event is below a particular threshold for acting on that particular type of event to reduce the potential impact of false positives, that is, the patient management unit 908 may only initiate automated adjustments to fluid delivery control parameters to respond to a particular type of event when the confidence value or probability of occurrence associated with that event output by the event detection unit 906 is greater than an actionability threshold value associated with that particular type of event. In this regard, the actionability threshold value may vary depending on the particular type of event, so that different types of events have different thresholds for actionability.

It should be noted that the gestured event detection process 1000 may be described in the context of a concurrent or real-time implementation, in practice, the gestured event detection process 1000 may be implemented in a sequential or prospective manner, for example, by the event detection unit 906 and/or the patient management unit 908 utilizing the current operational context to predict a future occurrence of an event and prospectively configuring or otherwise adjusting operation of a medical device in anticipation of the event. In this regard, based on the detected gesture data stream, the medical device may be subsequently reconfigured to account for the actual occurrence or absence of an event that was previously-predicted based on the patient's current operational context.

Figure 11:
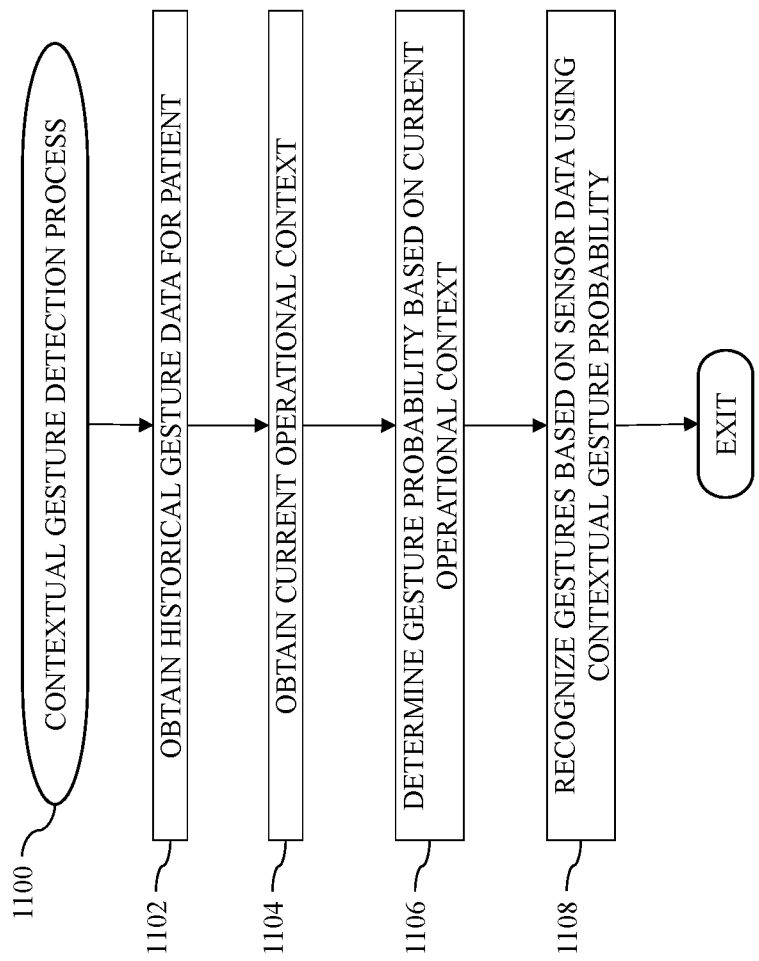
FIG. 11 is a flow diagram of an exemplary contextual gesture detection process in accordance with one or more exemplary embodiments.

FIG. 11 depicts an exemplary contextual gesture detection process 1100 suitable for implementation by a patient management system (e.g., patient management system 900) to recognize or otherwise resolve patient movements into gestures based on the current operational context. In this regard, the contextual gesture detection process 1100 may be implemented independently or in connection with the gestured event detection process 1000, depending on the particular application or embodiment. For example, the detected gestures and assigned probabilities (or confidence levels) determined in accordance with the contextual gesture detection process 1100 (e.g., at task 1108) may be output by the gesture recognition unit 904 in the patient management system 900 of FIG. 9 and function as an input to the event detection unit 906 implementing the gestured event detection process 1000 for detecting when the combination and/or sequence of detected gestures and associated probabilities confirms occurrence of a predicted event for the current operational context (e.g., task 1008) to thereby influence operation of a medical device or a medication delivery system 102 in a corresponding manner.

The various tasks performed in connection with the contextual gesture detection process 1100 may be performed by hardware, firmware, software executed by processing circuitry, or any combination thereof. For illustrative purposes, the following description refers to elements mentioned above in connection with FIGS. 1-9. It should be appreciated that the contextual gesture detection process 1100 may include any number of additional or alternative tasks, the tasks need not be performed in the illustrated order and/or the tasks may be performed concurrently, and/or the contextual gesture detection process 1100 may be incorporated into a more comprehensive procedure or process having additional functionality not described in detail herein. Moreover, one or more of the tasks shown and described in the context of FIG. 11 could be omitted from a practical embodiment of the contextual gesture detection process 1100 as long as the intended overall functionality remains intact.

The contextual gesture detection process 1100 begins by receiving or otherwise obtaining historical data for the patient, receiving or otherwise obtaining information characterizing the current operational context, and calculating or otherwise determining gesture probabilities based at least in part on the correlation between the current operational context and the historical operational context associated with past events, activities, or gestures for the patient (tasks 1102, 1104, 1106). For example, the gesture recognition unit 904 may retrieve or otherwise obtain the historical event data and/or historical gesture data associated with the patient from a database (e.g., database 114 via ancillary input 907) and analyze the historical event and/or gesture data to identify previous gestures that were previously detected or recognized for the patient. In this regard, in the absence of historical gesture data, past events may be mapped to corresponding gestures that would have been expected to be observed concurrent or contemporaneous to those events. Based on the timestamps and other contextual data associated with the patient's previous gestures (e.g., geolocation data, and/or the like), the gesture recognition unit 904 may calculate or otherwise determine the probability of the patient performing or otherwise exhibiting a particular type of gesture or activity at a particular time or within a particular window of time based the current operational context.

The contextual gesture detection process 1100 utilizes the gesture probability determined based on the current operational context to recognize, resolve or otherwise map received sensor data streams into detected gestures in a manner that accounts for the expected probability of a particular gesture occurring (task 1108). In this regard, the gesture recognition unit 904 may increase the confidence level or probability assigned to a detected gesture when the detected gesture is consistent with the patient's historical gestures correlated to the current operational context, or when the detected gesture otherwise corresponds to a gesture indicated by the current operational context. For example, if the patient historically performs food intake gestures or consumes meals at a particular time of day on a particular day of the week, the gesture recognition unit 904 may assign a greater confidence to a food intake gesture detected based on the sensor data stream received from the sensor unit(s) 902 at that particular time of day on that particular day of the week. Conversely, the gesture recognition unit 904 may decrease the confidence level or probability assigned to a detected gesture when the detected gesture is inconsistent with the patient's historical gestures correlated to the current operational context, or when the detected gesture otherwise corresponds to a gesture contraindicated by the current operational context. For example, if the patient historically does not perform food intake gestures or consume meals at a particular time of day on a particular day of the week, the gesture recognition unit 904 may assign a lower confidence to a detected food intake gesture at that particular time of day on that particular day of the week because the current operational context indicates that a food intake gesture at that particular time of day on that particular day of the week is more likely to be erroneous or a spurious movement by the patient. By increasing or decreasing the confidence or probability assigned to detected gestures in a manner that accounts for the current operational context, the downstream event detection unit 906 may assign greater or lesser weight to detected gestures to more accurately or reliably detect events consistent with the current operational context.

In yet other embodiments, the gesture recognition model(s) utilized by the gesture recognition unit 904 may be trained to receive as input variables, the probability of the patient performing or otherwise exhibiting a particular type of gesture derived based on the operational context. In such embodiments, the gesture recognition unit 904 may increasingly resolve sensor data in favor of a more probable gesture given the current operational context rather than other gestures that are less probable given the current operational context. For example, a sensor data stream that may not otherwise be resolvable into a potential type of gesture may be resolved into a food intake gesture at certain times of day or other operational contexts when the patient's historical behavior indicates the patient is more likely to experience a meal event, while at other times of day or different operational context the sensor data stream may be resolved into a different type of gesture or excluded from recognition due to the unlikelihood of a food intake gesture for those other operational contexts. By increasingly detecting gestures consistent with the current operational context (or filtering or deemphasizing gestures inconsistent with the current operational context), the downstream event detection unit 906 may more accurately or reliably detect events consistent with the current operational context.

Referring to FIG. 11 with reference to FIG. 10, it should be noted that in some embodiments, the gestured event detection process 1000 and the contextual gesture detection process 1100 may be implemented in connection with one another or otherwise be performed concurrently to improve the accuracy or reliability of both the gesture detection and the resulting event detection based on the current operational context. For example, based on the patient's historical data, the contextual gesture detection process 1100 may be performed by the gesture recognition unit 904 to increasingly recognize certain gestures or assign higher levels of confidence to certain gestures that are consistent with the patient's historical behavior based on correlations with the current operational context. The gestured event detection process 1000 may then be performed by the event detection unit 906 with respect to the contextually-adjusted gesture data stream provided by the gesture recognition unit 904 to increasingly detect certain events or assign higher levels of confidence to certain events that are consistent with the patient's historical behavior based on correlations with the current operational context.

Still referring to FIGS. 10-11, in some embodiments, the different operational contexts utilized to establish correlations between gestures or events may include temporal information pertaining to preceding events or gestures, that is, an operational context may be defined temporally by the duration of time that has elapsed since one or more preceding events or gestures. For example, when the patient's historical behavior indicates the patient is more likely to experience a meal event a certain time period (e.g., 30 minutes) after experiencing an exercise event, the gesture recognition unit 904 may increase the confidence level or probability assigned to a detected food intake gesture on when the current operational context corresponds to that time period after an exercise event. Likewise, when the patient's historical behavior indicates a particular type of event is more likely within some period of time after a preceding event of a different type, the event detection unit 906 may increase the confidence level or probability assigned to that particular type on when the current operational context corresponds to that time period after such a preceding event. Similarly, when the patient's historical behavior indicates a particular event attributes are more likely based on a temporal or sequential relationship to a preceding event, the event detection unit 906 may modify or adjust the predicted attributes for a gestured event to account for the likely event attributes indicated by the patient's historical behavior when the current operational context corresponds to that time period after such a preceding event. In this manner, preceding events or gestures may inform subsequently detected events or gestures. For example, the output of the event detection unit 906 may be fed back as an auxiliary input 905 to the gesture recognition unit 904 for detecting gestures in the future based on a preceding gestured event and the current operational context and/or as an auxiliary input 907 to the event detection unit 906 for detecting gestured events in the future based on a preceding gestured event and the current operational context. Similarly, the output of the gesture recognition unit 904 may be fed back as an auxiliary input 905 to the gesture recognition unit 904 for detecting gestures in the future based on one or more preceding gestures and the current operational context and/or provided as an auxiliary input 907 to the event detection unit 906 for detecting gestured events in the future based on one or more preceding gestures and the current operational context.

Referring to FIG. 1 with reference to FIGS. 9-11, a medication dosing and dispensing system ("MDDS") such as system 100 that includes a medication delivery device 102 that regulates delivery of medication to a user in concert with a gesture-based detection system 104 may analyze historical patient data maintained in a database 114 to predict when certain events or activities are likely to occur based on the operational context and perform contextual delivery adjustments that are responsive to or otherwise informed by detected gestures. For example, an MDDS may predict the occurrence of food intake events, exercise events, sleep events and/or the like based on the historical patient data using the contextual data associated with historical occurrences of those events (e.g., based on recorded timestamps or time of day, day of the week, duration of the event, geographic location, etc.), other characteristics or attributes of those events (e.g., meal content, meal size, exercise intensity, sleep quality, etc.), potentially other data concurrent or contemporaneous to those events (e.g., sensor glucose measurement data, heart rate measurement data, calendar information, emotional state indicators, and/or the like), and/or temporal or sequential relationships to occurrence of other historical events.

As one example, an MDDS may predict the occurrence of an exercise event in relation to the occurrence of a food intake event, for example, that a patient will start to exercise within a certain time window after the start or end of a food intake event. The MDDS may also assign a confidence level to that prediction. For example, when the start of a food intake event is detected, an MDDS may predict with an 85% confidence level that a patient will start to exercise within 30 minutes. Thus, when the current operational context corresponds to within 30 minutes of a preceding food intake event, the gesture recognition unit 904 may assign a confidence value or probability of 85%, for example, to any exercise gestures detected within that time period based on the current operational context and/or the event detection unit 906 may assign a confidence value or probability of 85%, for example, to any exercise events detected based on the output of the gesture recognition unit 904 within that time period based on the current operational context. By increasing the confidence associated with the detected gestured event input to the patient management unit 908, the patient management unit 908 may respond more aggressively or proportionally to the detect occurrence of an event consistent with the patient's historical contextual behavior. The MDDS may also predict additional characteristics of the probable exercise event based on the patient's historical data, such as, a probable duration of exercise, type of exercise, intensity of exercise, and expected ranges for the patient's physiological measurement data (e.g., expected glucose levels, heart rate measurements, and/or the like). In this manner, the MDDS may adjust a medication dosing and/or medication dispensing schedule in response to a detected gestured event based on the current operational context. For example, if the MDDS is an insulin therapy system, the patient management unit 308 may determine a reduced insulin dosage or relaxed insulin delivery schedule, or the patient management unit 308 may increase the target glucose value or reference glucose level used to determine insulin dosage commands (e.g., by a closed-loop control system) in a manner that is commensurate or proportional to the confidence level assigned a detected exercise event. In an equivalent manner, for a detected food intake event, the patient management unit 308 may determine an increased insulin dosage or a more aggressive insulin delivery schedule, or the patient management unit 308 may decrease the target glucose value or reference glucose level used to determine insulin dosage commands in a manner that is commensurate or proportional to the confidence level/value assigned a detected food intake event.

As another example, an MDDS may predict the start of a sleep event in relation to the occurrence of a food intake event. For example, an MDDS may predict that a patient will go to sleep within a certain time window after the start or end of a certain food intake event. An MDDS may make such a prediction and assign a confidence level to that prediction. For example, when the end of a food intake event is detected, an MDDS may predict with a 95% confidence level that a patient will go to bed within 1 hour. The MDDS may also predict additional characteristics of the imminent sleep event such as for example duration, quality or range of blood glucose levels. Thereafter, in the absence of particular gestures or physical a movement within an hour of a food intake event, based on the current operational context, the event detection unit 306 may detect a probable sleep event and assign the sleep event with a 95% confidence level based on the patient's historical behavior for the current operational context. The patient management unit 308 may then adjust medication dosing and/or a medication dispensing schedule in a manner commensurate with the 95% confidence level. For example, if the MDDS is an insulin therapy system, the patient management unit 308 may reduce the insulin dosing or it may increase the target glucose value or reference glucose level used to determine insulin dosage commands to reduce insulin dosage or delivery. Conversely, when the output of the gesture recognition unit 904 and/or the event detection unit 306 indicates the absence of a sleep event, the patient management unit 308 may respond in the opposite manner to account for the probable absence of a sleep event.

In one or more embodiments, the current operational context may be utilized to detect a particular social setting or otherwise activate a particular automated control mode, such that detected gestures and/or gestured events are handled in a manner that reflects the particular social setting or operational context, that is, when the current time of day, day of the week, geographic location, and the like may indicate that the patient is at a party or other social setting where certain gestures or events are likely to deviate from the patient's normal or historical behavior. Nonlimiting examples of a social setting include: a restaurant, a bar, a night club, an entertainment venue, a party, a wedding, a social gathering, a sporting event, and a concert. For example, at a party, wedding, or other social gathering, frequent food intake gestures may correspond to a patient eating appetizers, finger foods or the like rather than consuming a larger meal, or frequent drinking gestures may correspond to a patient consuming an alcoholic beverage rather than water. Accordingly, the event detection unit 906 may utilize the current operational context received via the auxiliary input 907 to adjust the attributes or characteristics associated with a gestured event based on the current social setting, or otherwise alter the event output data provided to the patient management unit 908 to cause the patient management unit 908 to respond to a gestured event in a manner that accounts for the current social setting to achieve better glycemic control. For example, when the current geographic location indicates the patient is at a bar or nightclub, the event detection unit 906 may respond to food intake gestures or drinking gestures in a manner that reflects the current operational context corresponding to a social setting rather than responding as the event detection unit 906 otherwise would if the current operational context indicated more normal patient behavior (e.g., where the geographic location corresponds to the patient's home).

In one or more embodiments, the event detection unit 906 may be trained based on correlations between the number and/or frequency of food intake gestures and corresponding food items and portion sizes to estimate attributes associated with a food intake event predicted based on detected food intake gestures in a given social setting. For example, the number and/or frequency of bites for a particular food item from a food library may be mapped to an estimated amount of carbohydrates or other nutritional content per bite for that food item. Thereafter, when the current operational context indicates a particular type of social setting, the event detection unit 906 may analyze the detected gesture data stream output by the gesture recognition unit 904 to map the food intake gestures to a particular type of food item given the current social setting, and then output the estimated amount of carbohydrates per bite or other estimated attributes of the food intake event given the current social setting to the patient management unit 908 so that the patient management unit 908 adjusts insulin dosage commands and/or insulin delivery schedules in a manner that accounts for the current social setting.

In yet other embodiments, the current geographic location or other operational context variables (e.g., wireless local area network name or connectivity state, and/or the like) may be mapped to a particular setting or control mode that influences operation of the event detection unit 906 and/or the patient management unit 908 in a corresponding manner. In this regard, in response to detecting a social setting based on the current operational context, the event detection unit 906 and/or the patient management unit 908 may automatically initiate operation in an alternative control mode that accounts for the current social setting. For example, the event detection unit 906 and/or the patient management unit 908 may be configured to support a social mode that is activated based on the current operational context to account for food intake gestures, drinking gestures, or other gestures that are likely to deviate from normal characteristics based on the current social setting (e.g., when the current geographic location corresponds to a buffet restaurant, a bar, a night club, or other social gathering venue). For example, when the event detection unit 906 detects a gestured food intake event for a particular type of social setting, the event detection unit 906 may command, instruct, or otherwise signal the patient management unit 908 to enter into a social mode to adjust the manner in which the patient management unit 908 determines dosage commands or delivery schedules in response to a gestured food intake event. In the social mode, the patient management unit 908 may be configured to generate or otherwise command bolus dosages in an open-ended manner on a per food intake event or per food intake gesture basis, for example, by administering an insulin bolus dosage amount determined based on an estimated amount of carbohydrate per bite or another estimated event attribute for the current social setting. Additionally, or alternatively, the number, timing and/or frequency of the detected food intake gestures may be analyzed to determine the estimated meal size, the estimated meal duration, and the like, which, in turn may be utilized by the patient management unit 908 to dynamically adjust insulin delivery and/or therapy in a corresponding manner that reflects both the current social setting or context as well as the number, timing and/or frequency of the detected food intake gestures in that particular setting. In some examples, patient management unit 908 enters into a buffet mode that operates similar to the social mode that generates or otherwise commands bolus dosages in an open-ended manner on a per food intake event or per food intake gesture basis. In some examples, patient management unit 908 enters the buffet mode when the current location of the user is associated with a restaurant and/or when a threshold number of eating or drinking gestures are detected within a threshold period of time.

For example, during normal operation of an MDDS, a gesture-based detection system 104 may detect a meal event or other food intake event and inform the control algorithm of a medication delivery system 102 associated with an infusion device to initiate or perform actions that mitigate postprandial hyperglycemia while alleviating patient burdens such as carbohydrate counting, manual pre-bolusing, and/or the like. For example, a closed-loop glucose control system or other autonomous control system (e.g., patient management unit 908) may respond to a gestured food intake event by automatically decreasing a setpoint or target glucose value (e.g., target glucose setpoint value 322) to increase basal insulin delivery, automatically increasing an upper insulin delivery limit for automated basal insulin delivery to allow more insulin to be delivered, and/or automatically delivering a bolus of insulin responsive to the gestured food intake event (where the bolus insulin dosage may reflect estimated attributes for the food intake event, the confidence level assigned to the gestured food intake event, and/or the like). In this regard, in a social or buffet mode, the closed-loop glucose control system or other autonomous control system may be configured to increase the temporary duration of time for which the adjusted target glucose value and/or adjusted insulin delivery limits are utilized to account for the open-ended or indefinite nature of the potential food intake event, or the patient management unit 908 may otherwise alter the manner in which target glucose value and/or the insulin delivery limits are adjusted to respond to a gestured food intake event with a desired level of aggressiveness for the current social or meal setting.

Figure 12:
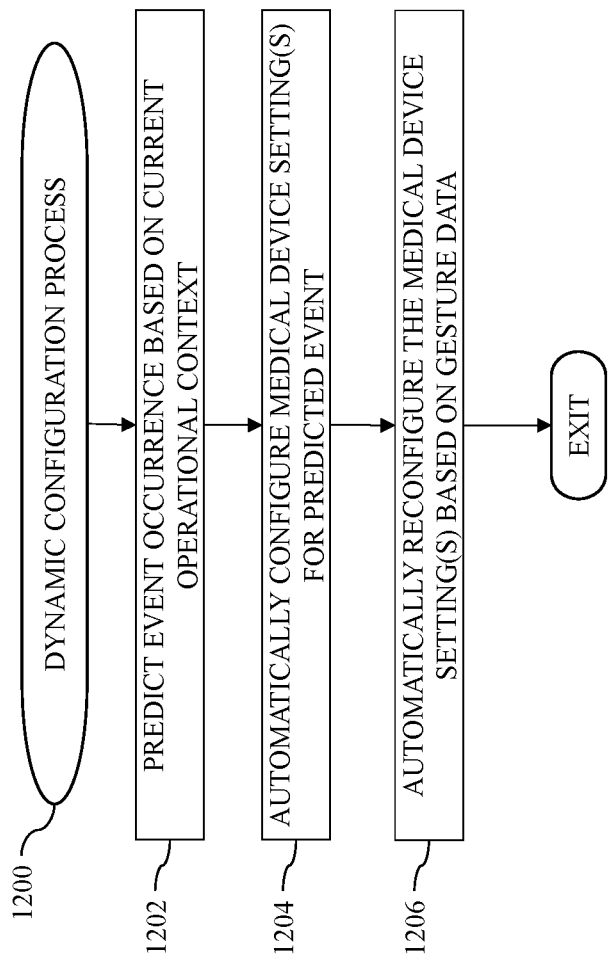
FIG. 12 is a flow diagram of an exemplary dynamic configuration process in accordance with one or more exemplary embodiments.

FIG. 12 depicts an exemplary dynamic configuration process 1200 suitable for implementation by a patient management system to dynamically adjust medical device operation when subsequent gesture data confirms or contraindicates occurrence of a predicted event. In this regard, the dynamic configuration process 1200 may be implemented independently or in connection with the gestured event detection process 1000 and/or the contextual gesture detection process 1100, depending on the particular application or embodiment. The various tasks performed in connection with the dynamic configuration process 1200 may be performed by hardware, firmware, software executed by processing circuitry, or any combination thereof. For illustrative purposes, the following description refers to elements mentioned above in connection with FIGS. 1-9. It should be appreciated that the dynamic configuration process 1200 may include any number of additional or alternative tasks, the tasks need not be performed in the illustrated order and/or the tasks may be performed concurrently, and/or the dynamic configuration process 1200 may be incorporated into a more comprehensive procedure or process having additional functionality not described in detail herein. Moreover, one or more of the tasks shown and described in the context of FIG. 12 could be omitted from a practical embodiment of the dynamic configuration process 1200 as long as the intended overall functionality remains intact.

The dynamic configuration process 1200 initializes or otherwise begins by predicting the occurrence of an event and automatically configuring one or more settings of a medical device to account for the probable occurrence of the event (tasks 1202, 1204). For example, based on the current operational context, a meal event or other food intake event may be predicted, and in response, the patient management unit 908 or other control system associated with an infusion device (e.g., patient care application 110, closed loop glucose control system 300, controller 310, or the like) may automatically decrease the target glucose setpoint value (e.g., target glucose setpoint value 322) and/or automatically increase an upper insulin delivery limit by some initial amount to facilitate increased automated basal insulin delivery. In practice, the initial amount of adjustments to the device settings may be limited for safety purposes, for example, to account for potential measurement errors or uncertainty associated with the event prediction.

After initially configuring the device setting(s) for the predicted event occurrence, the dynamic configuration process 1200 automatically reconfigures or readjusts the device setting(s) based on whether subsequent gesture data confirms or contraindicates the predicted event occurrence (task 1206). In this regard, the gesture data stream output by the gesture recognition unit 904 may be analyzed or otherwise utilized to increase or decrease the confidence associated with the predicted event occurrence to increase or decrease the initial adjustment(s) to the device setting(s) in a corresponding manner. For example, if a food intake is initially predicted with a confidence of 50% based on the current operational context (e.g., the current time of day corresponds to when the patient typically consumes a meal), the target glucose setpoint value may be initially decreased by an initial amount corresponding to a product of the confidence level and a maximum amount of setpoint adjustment (e.g., one half the maximum amount of setpoint adjustment). Thereafter, when the gesture data stream output by the gesture recognition unit 904 includes one or more food intake gestures that cause the event detection unit 906 to predict or detect occurrence of a food intake event with a confidence of 80%, for example, the patient management unit 908 may automatically reconfigure the target glucose setpoint value by decreasing the target glucose setpoint value from its initial unadjusted or nominal value by an increased amount of adjustment corresponding to 80% of the maximum amount of setpoint adjustment, thereby allowing a glucose control system (e.g., closed loop glucose control system 300) to more aggressively respond to an increase in the patient's sensor glucose measurement values when the detected gestures confirm the predicted event occurrence. It should be noted that the subject matter is not limited to target glucose setpoint adjustments and can be implemented in an equivalent manner for any number of different delivery control parameters, such as, for example, upper insulin delivery limits, maximum basal insulin delivery rates, bolus targets, active insulin time, and/or the like.

The dynamic configuration process 1200 may also be performed to reconfigure medical device setting(s) to mitigate previous predictive adjustments in response to non-occurrence of a predicted event. In this regard, non-activity can reduce the insulin absorption rate, where a subsequent change in activity can cause a decrease in glucose levels as previously administered insulin is increasingly absorbed. Accordingly, the dynamic configuration process 1200 may be performed by the patient management unit 908 or other infusion device control system to automatically reconfigure device setting(s) when the gesture data indicates inactivity by the patient (e.g., task 1206) to prevent stacking of insulin in an inactive state. For example, based on the current operational context, the dynamic configuration process 1200 may initially adjust one or more fluid delivery setting(s) or other setting(s) to account for a predicted event or other level of activity by the patient (e.g., tasks 1202, 1204). Thereafter, when the gesture data stream output by the gesture recognition unit 904 indicates the absence of the expected event or activity, the event detection unit 906 may correspondingly decrease the confidence level associated with the event to cause the patient management unit 908 to automatically reconfigure the fluid delivery setting(s) or other device setting(s) to account for inactivity and mitigate the initial predictive adjustments to the device setting(s).

It should be noted that the dynamic configuration process 1200 may also be implemented in an equivalent manner to dynamically adjust user notification or alert settings, or other aspects of device operation or patient management independent of fluid delivery. For example, based on the current operational context, one or more alert settings may be adjusted to account for the current social setting or other predictions (e.g., to increase and/or decrease the frequency or intensity of alerting). User notifications may be generated, suppressed, or otherwise influenced by the initial prediction(s) while the current operational context and/or gesture data is consistent with the initial prediction. In some embodiments, the user notifications may include one or more automated alerts that indicate a recommended bolus amount to account for a gestured event given the current social setting, a recommended time (or window of time) for when a bolus should be delivered, a recommended bolus amount to pre-bolus or otherwise prospectively account for a predicted future event based on the current social setting and/or recent gestured events (e.g., a predicted future meal or other food intake event based on the current social and detection of a gestured exercise event), a recommended time (or window of time) for when a pre-bolus should be delivered to account for the predicted future event, and/or the like. Thereafter, when the gesture data contraindicates the initial prediction regarding the social setting, event occurrence or other patient activity, the dynamic configuration process 1200 may dynamically reconfigure the alert settings to increase and/or decrease the frequency or intensity of alerting to account for the current gesture data and generate or suppress user notifications in a corresponding manner that reflects the patient's current physical movements or activity state substantially in real-time.

As yet another example, the dynamic configuration process 1200 may be configured to automatically reconfigure insulin bolus dosage amounts for automatic delivery on a per-food intake gesture or per-bite basis. Based on the patient's historical data and correlations between the patient's historical meal data and contemporaneous or concurrent historical gesture data, an expected number of bites and an expected number of carbohydrates per bite may be determined. For example, the patient is predicted to consume a meal having 40 grams of carbohydrates (e.g., based on the correlation between the current operational context and the patient's historical meal data), and the patient is predicted to perform 20 bites (e.g., based on correlations with the patient's historical gesture data), the patient may be expected to consume 2 grams of carbohydrates per food intake gesture, which may be divided by the patient's carbohydrate ratio to obtain an estimated bolus dosage per food intake gesture. In this regard, the patient management system 308 may be initially configured to automatically command or schedule a bolus dosage of insulin corresponding to the estimated bite size (e.g., 2 grams per food intake gesture divided by the patient's carbohydrate ratio) in response to a food intake event indicated by the unit 306. Thereafter, the bolus dosage amount may be dynamically reconfigured or other fluid delivery control parameters may be adjusted when the patient's gesture data deviates from the initial prediction. For example, the number or frequency of food intake gestures may indicate a smaller or larger estimated bite size and/or a smaller or larger meal size, and in response, the patient management system 308 automatically reconfigure the bolus dosage amount or adjust other delivery control parameters (e.g., target glucose setpoint value, or the like). In this regard, the patient's current or real-time glucose measurement data may be utilized in connection with the gesture data to dynamically reconfigure infusion device operation. For example, when the patient's glucose measurement data is declining or trending negative, the per bite bolus dosage amount may be dynamically decreased or disabled to mitigate potential hypoglycemia. As another example, the patient's total daily dose or other patient-specific parameters may be utilized to calculate a lower maximum per bite bolus dosage amount to be utilized in lieu of the initially estimated bolus dosage amount. In this regard, any number of mitigations may be utilized to avoid hypoglycemia (e.g., increasing the target glucose setpoint value), and the subject matter described herein is not intended to be limited to any particular type, number, or configuration of mitigations that may be dynamically reconfigured by the dynamic configuration process 1200.

It should be appreciated the subject matter described herein allows for correlations between a patient's historical meal data or other historical event data, historical insulin delivery data, historical glucose measurement data, historical gesture data, historical contextual data, and/or the like to be analyzed and leveraged to predict the timing and/or occurrence of different events based on the current, real-time operational context and temporal relationship to preceding events and/or gestures by the patient. In this manner, gesture data or gestured event predictions can be utilized to inform event predictions or detection, dynamically adjust medical device operation, or inform future detection or prediction of gestures or events, while also accounting for the likely influence of the current social setting or other operational context. By using the current operational context and gesture data in combination, confidence in events predicted or detected based on gestures can be increased, thereby allowing for dynamic adjustments for improved glycemic control. False positives or non-occurrence of predictions can also be accounted for and mitigated, thereby improving safety.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a medical device using a sensing arrangement capable of detecting physical movement by a patient, the method comprising:
identifying, by a control system associated with the medical device, a current operational context;
predicting, by the control system, an occurrence of an event based at least in part on historical data associated with the patient and a correlation between the current operational context and the event, resulting in a predicted occurrence of the event;
automatically configuring operation of the medical device to make an adjustment to insulin delivery by the medical device to account for the predicted occurrence of the event; and
after configuring the operation of the medical device to account for the predicted occurrence of the event, automatically reconfiguring the operation of the medical device to:
increase the adjustment to the insulin delivery by the medical device in response to detected gesture data influenced by an output of the sensing arrangement confirming the occurrence of the event; or
mitigate the adjustment to the insulin delivery by the medical device in response to the detected gesture data contradicting the predicted occurrence of the event.

2. The method of claim 1, wherein:
the medical device comprises an insulin delivery device;
automatically configuring the operation of the medical device comprises adjusting a delivery control parameter in a manner that is influenced by a first confidence value associated with the predicted occurrence of the event; and
automatically reconfiguring the operation of the medical device comprises readjusting the delivery control parameter in a manner that is influenced by a second confidence value influenced by the detected gesture data.

3. The method of claim 2, wherein:
adjusting the delivery control parameter comprises adjusting the delivery control parameter to increase delivery of insulin by the insulin delivery device based on the predicted occurrence of the event; and
readjusting the delivery control parameter comprises adjusting the delivery control parameter to further increase delivery of insulin when the second confidence value is greater than the first confidence value.

4. The method of claim 2, wherein:
adjusting the delivery control parameter comprises adjusting the delivery control parameter to increase delivery of insulin by the insulin delivery device based on the predicted occurrence of the event; and
readjusting the delivery control parameter comprises adjusting the delivery control parameter to decrease delivery of insulin when the second confidence value is less than the first confidence value.

5. The method of claim 2, wherein:
adjusting the delivery control parameter comprises adjusting the delivery control parameter to decrease delivery of insulin by the insulin delivery device based on the predicted occurrence of the event; and
readjusting the delivery control parameter comprises adjusting the delivery control parameter to further decrease delivery of insulin when the second confidence value is greater than the first confidence value.

6. The method of claim 2, wherein:
adjusting the delivery control parameter comprises adjusting the delivery control parameter to decrease delivery of insulin by the insulin delivery device based on the predicted occurrence of the event; and
readjusting the delivery control parameter comprises adjusting the delivery control parameter to increase delivery of insulin when the second confidence value is less than the first confidence value.

7. The method of claim 1, further comprising:
detecting a social setting based on the current operational context; and
predicting an attribute of the event of the predicted occurrence of the event based at least in part on the social setting, wherein automatically configuring the operation of the medical device comprises automatically configuring the operation of the medical device based at least in part on the predicted attribute.

8. The method of claim 1, further comprising detecting a social setting based on the current operational context, wherein automatically configuring the operation of the medical device comprises automatically initiating the operation of the medical device in an alternative mode based at least in part on the social setting.

9. The method of claim 8, wherein the social setting comprises a restaurant, a bar, a night club, an entertainment venue, a party, a wedding, or a social gathering.

10. The method of claim 9, wherein the alternative mode comprises a buffet mode.

11. At least one non-transitory computer readable medium having stored thereon program code instructions that are configurable to cause at least one processor to perform a method comprising:
identifying a current operational context associated with operating a medical device capable of influencing a physiological condition of a patient;
predicting an occurrence of an event based at least in part on historical data associated with the patient and a correlation between the current operational context and the event, resulting in a predicted occurrence of the event;
automatically configuring operation of the medical device to make an adjustment to insulin delivery by the medical device to account for the predicted occurrence of the event; and
after configuring the operation of the medical device to account for the predicted occurrence of the event, automatically reconfiguring the operation of the medical device to:
increase the adjustment to the insulin delivery by the medical device in response to detected gesture data influenced by an output of a sensing arrangement capable of detecting physical movement by the patient confirming the occurrence of the event; or
mitigate the adjustment to the insulin delivery by the medical device in response to the detected gesture data contradicting the predicted occurrence of the event.

12. The at least one non-transitory computer readable medium of claim 11, wherein:

the medical device comprises an insulin delivery device;
automatically configuring the operation of the medical device comprises adjusting a delivery control parameter in a manner that is influenced by a first confidence value associated with the predicted occurrence of the event; and
automatically reconfiguring the operation of the medical device comprises readjusting the delivery control parameter in a manner that is influenced by a second confidence value influenced by the detected gesture data.

13. The at least one non-transitory computer readable medium of claim 11, wherein the method further comprises:
detecting a social setting based on the current operational context; and
predicting an attribute of the event of the predicted occurrence of the event based at least in part on the social setting, wherein automatically configuring the operation of the medical device comprises automatically configuring the operation of the medical device based at least in part on the predicted attribute.

14. The at least one non-transitory computer readable medium of claim 11, wherein the method further comprises detecting a social setting based on the current operational context, wherein automatically configuring the operation of the medical device comprises automatically initiating the operation of the medical device in an alternative mode based at least in part on the social setting.

15. A system comprising:
a medical device that regulates delivery of insulin to a patient;
a gesture detection system configured to generate gesture data for the patient, and configured to communicate the gesture data; and
at least one controller that controls operation of the medical device, the at least one controller configured to:
identify a current operational context;
predict an occurrence of an event based at least in part on historical data associated with the patient and a correlation between the current operational context and the event, resulting in a predicted occurrence of the event;
automatically configure a setting of the medical device for delivering insulin to the patient based on the predicted occurrence of the event; and
after configuring the setting of the medical device based on the predicted occurrence of the event, automatically reconfiguring the setting of the medical device based on the gesture data received from the gesture detection system to:
more aggressively configure the setting of the medical device for delivering insulin in response to the gesture data confirming the occurrence of the event; or
mitigate the configuring of the setting of the medical device in response to the gesture data contradicting the predicted occurrence of the event.

16. The system of claim 15, wherein:
the medical device comprises an insulin delivery device;
the setting comprises a delivery control parameter; and
the at least one controller is configured to automatically configure the delivery control parameter in a manner that is influenced by a first confidence value associated with the predicted occurrence of the event and thereafter automatically reconfigure the delivery control parameter in a manner that is influenced by a second confidence value influenced by the gesture data.

17. The system of claim 16, wherein:
the at least one controller is configured to automatically configure the delivery control parameter to increase delivery of insulin by the insulin delivery device based on the predicted occurrence of the event; and
the at least one controller is configured to automatically reconfigure the delivery control parameter to further increase delivery of insulin when the second confidence value is greater than the first confidence value.

18. The system of claim 16, wherein:
the at least one controller is configured to automatically configure the delivery control parameter to increase delivery of insulin by the insulin delivery device based on the predicted occurrence of the event; and
the at least one controller is configured to automatically reconfigure the delivery control parameter to decrease delivery of insulin when the second confidence value is less than the first confidence value.

19. The system of claim 16, wherein:
the at least one controller is configured to automatically configure the delivery control parameter to decrease delivery of insulin by the insulin delivery device based on the predicted occurrence of the event; and
the at least one controller is configured to automatically reconfigure the delivery control parameter to further decrease delivery of insulin when the second confidence value is greater than the first confidence value.

20. The system of claim 16, wherein:
the at least one controller is configured to automatically configure the delivery control parameter to decrease delivery of insulin by the insulin delivery device based on the predicted occurrence of the event; and
the at least one controller is configured to automatically reconfigure the delivery control parameter to increase delivery of insulin when the second confidence value is less than the first confidence value.

* * * * *